US010733741B2

(12) United States Patent
Watanabe

(10) Patent No.: US 10,733,741 B2
(45) Date of Patent: Aug. 4, 2020

(54) INFORMATION PROCESSING DEVICE, INFORMATION PROCESSING METHOD, PROGRAM, AND INFORMATION PROCESSING SYSTEM

(71) Applicant: Sony Corporation, Tokyo (JP)

(72) Inventor: Shinji Watanabe, Tokyo (JP)

(73) Assignee: Sony Corporation, Tokyo (JP)

(*) Notice: Subject to any disclaimer, the term of this patent is extended or adjusted under 35 U.S.C. 154(b) by 97 days.

(21) Appl. No.: 15/773,001

(22) PCT Filed: Nov. 4, 2016

(86) PCT No.: PCT/JP2016/082809
§ 371 (c)(1),
(2) Date: May 2, 2018

(87) PCT Pub. No.: WO2017/082167
PCT Pub. Date: May 18, 2017

(65) Prior Publication Data
US 2018/0330510 A1 Nov. 15, 2018

(30) Foreign Application Priority Data
Nov. 11, 2015 (JP) ................ 2015-221330

(51) Int. Cl.
G06T 7/246 (2017.01)
G16B 45/00 (2019.01)
(Continued)

(52) U.S. Cl.
CPC .......... G06T 7/251 (2017.01); G06K 9/00127 (2013.01); G06T 5/003 (2013.01);
(Continued)

(58) Field of Classification Search
None
See application file for complete search history.

(56) References Cited

U.S. PATENT DOCUMENTS 6,353,683 B1 * 3/2002 Horiike ................ G06T 9/004
348/699
8,902,306 B2 12/2014 Mimura et al.
(Continued)

FOREIGN PATENT DOCUMENTS

JP  2003-250804 A  9/2003
JP  2004-118485 A  4/2004
(Continued)

OTHER PUBLICATIONS

Saeed Anwar, Cong Phuoc Huynh, Fatih Porikli; "Class-Specific Image Deblurring"; The IEEE International Conference on Computer Vision (ICCV), Dec. 2015, pp. 495-503 (Year: 2015).*
(Continued)

Primary Examiner — Kim Y Vu
Assistant Examiner — Nathan J Bloom
(74) Attorney, Agent, or Firm — Wolf, Greenfield & Sacks, P.C.

(57) ABSTRACT

According to some aspects, an information processing device is provided. The information processing device includes circuitry configured to set at least one region of an image of a biological sample and select a motion compensation parameter calculated based at least on a motion of the at least one region. The circuitry is further configured to control display of a result of performing a process on the at least one region using the selected motion compensation parameter.

21 Claims, 14 Drawing Sheets

(51) Int. Cl.
    *G06T 5/00*      (2006.01)
    *G06T 5/50*      (2006.01)
    *G06K 9/00*      (2006.01)
    *G06T 7/207*     (2017.01)
    *G06T 7/11*      (2017.01)

(52) U.S. Cl.
    CPC .................. *G06T 5/50* (2013.01); *G06T 7/11* (2017.01); *G06T 7/207* (2017.01); *G06T 7/246* (2017.01); *G16B 45/00* (2019.02); *G06T 2207/10016* (2013.01); *G06T 2207/10056* (2013.01); *G06T 2207/20201* (2013.01); *G06T 2207/30024* (2013.01)

(56) References Cited

U.S. PATENT DOCUMENTS

| | | | |
|---|---|---|---|
| 2005/0185824 A1* | 8/2005 | Chen | G06K 9/3241 382/103 |
| 2006/0028552 A1* | 2/2006 | Aggarwal | G01S 5/16 348/169 |
| 2007/0052803 A1* | 3/2007 | Chosak | G06K 9/00771 348/143 |
| 2008/0225125 A1* | 9/2008 | Silverstein | H04N 5/2353 348/208.4 |
| 2008/0279431 A1* | 11/2008 | Kitamura | A61B 1/00009 382/128 |
| 2010/0249592 A1 | 9/2010 | Langeland et al. | |
| 2012/0062732 A1* | 3/2012 | Marman | H04N 7/18 348/142 |
| 2014/0341474 A1* | 11/2014 | Dollar | G06K 9/00711 382/197 |
| 2018/0309940 A1* | 10/2018 | Okada | G06T 5/007 |
| 2019/0200032 A1* | 6/2019 | Iwamoto | H04N 5/23245 |

FOREIGN PATENT DOCUMENTS

| | | |
|---|---|---|
| JP | 2005-102082 A | 4/2005 |
| JP | 2006-075590 A | 3/2006 |
| JP | 2007-334746 A | 12/2007 |
| JP | 2010-525299 A | 7/2010 |

OTHER PUBLICATIONS

S. Anwar, F. Porikli and C. P. Huynh, "Category-Specific Object Image Denoising," in IEEE Transactions on Image Processing, vol. 26, No. 11, pp. 5506-5518, Nov. 2017. (Year: 2017).*

J. Pan, W. Ren, Z. Hu and M. Yang, "Learning to Deblur Images with Exemplars," in IEEE Transactions on Pattern Analysis and Machine Intelligence, vol. 41, No. 6, pp. 1412-1425, Oct. 2018 (Year: 2018).*

International Preliminary Report on Patentability dated May 24, 2018 in connection with International Application No. PCT/JP2016/082809.

International Search Report and Written Opinion dated Feb. 7, 2017 in connection with International Application No. PCT/JP2016/082809.

Anonymous: CellTrack—An Open-Source Software for Cell Tracking and Motility Analysis (project website), Jun. 25, 2015 (Jun. 25, 2015), Database Research Group. Department of Computer Science and Engineering, The Ohio State University, pp. 1-9, XP55331318, Retrieved from the internet: URL:http://web.archive.org/web/20150625041010/http://bio.cse.ohio-state.edu/CellTrack/, retrieved on Dec. 22, 2016.

Japanese Office Action dated Sep. 3, 2019 in connection with Japanese Application No. 2015-221330, and English translation thereof.

* cited by examiner

[Fig. 1]
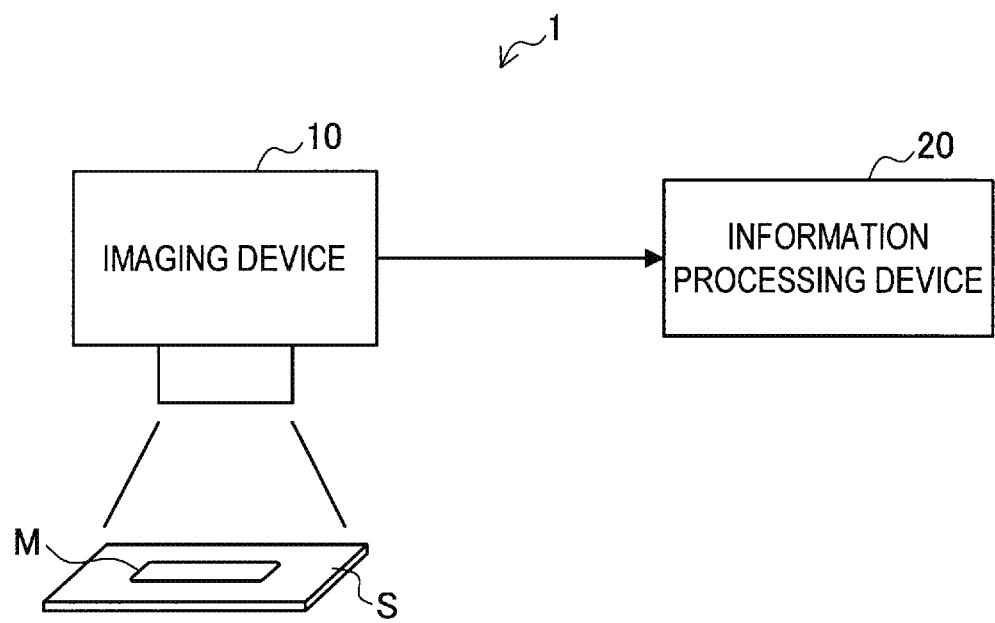

[Fig. 2]
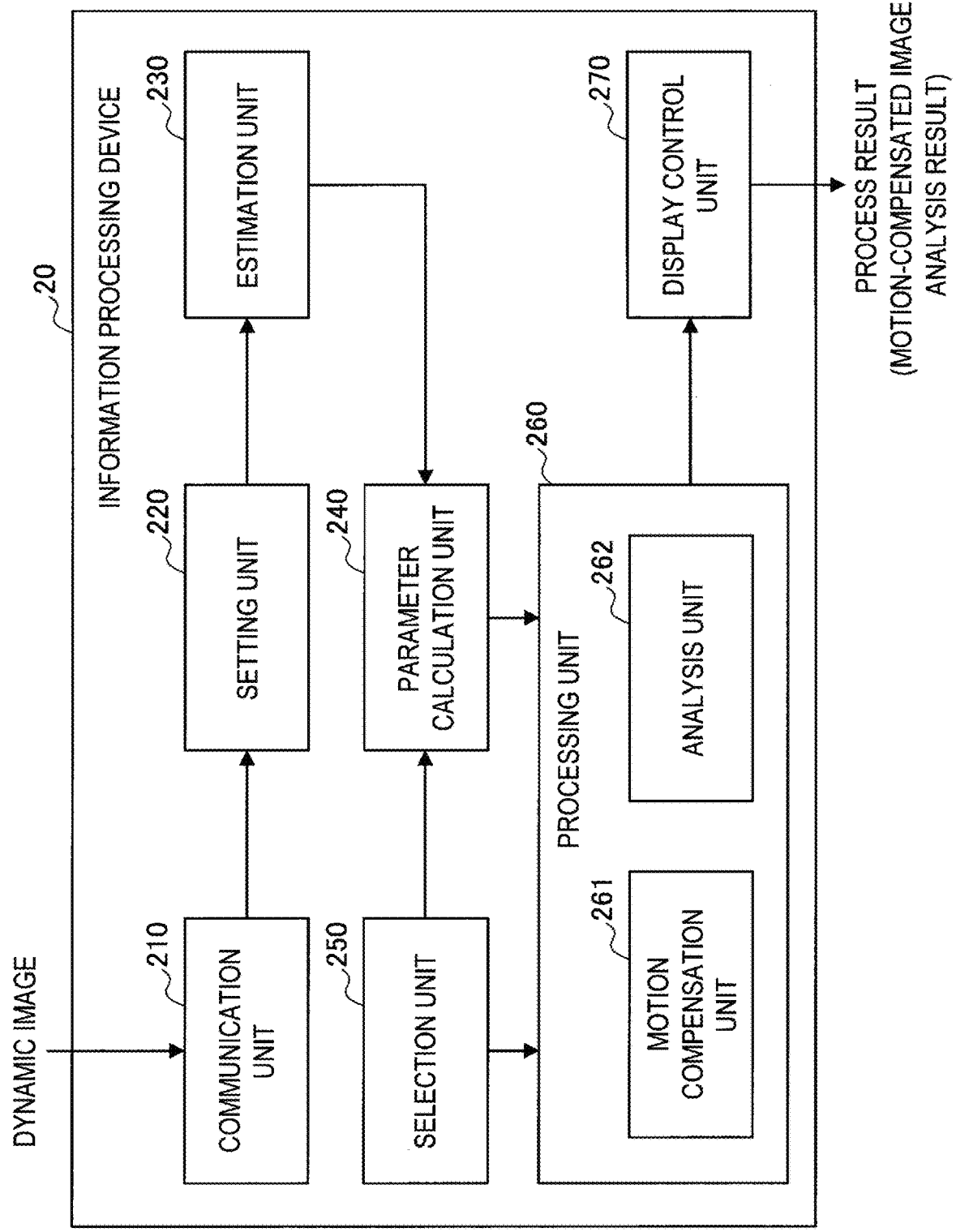

[Fig. 3]
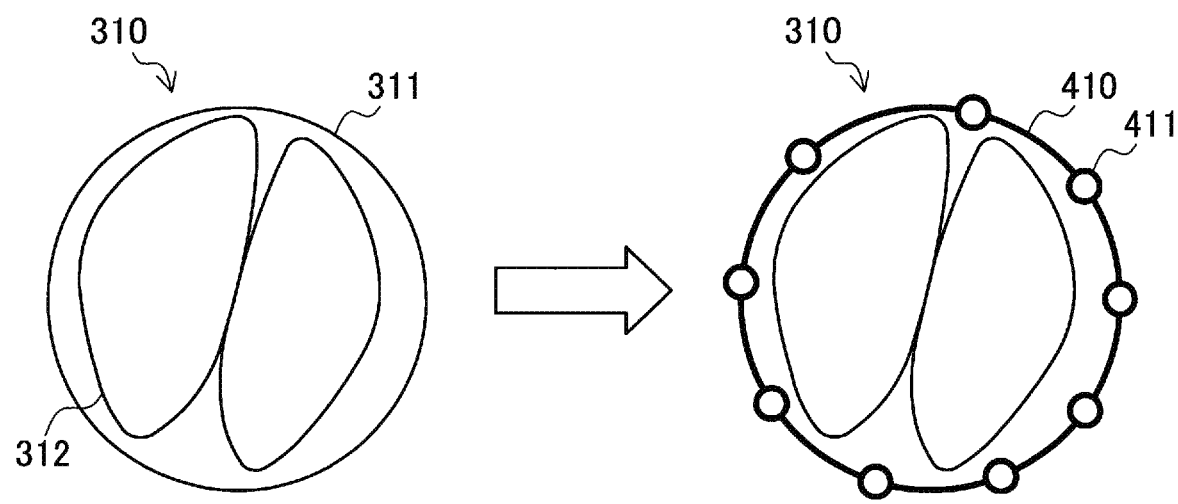

[Fig. 4]
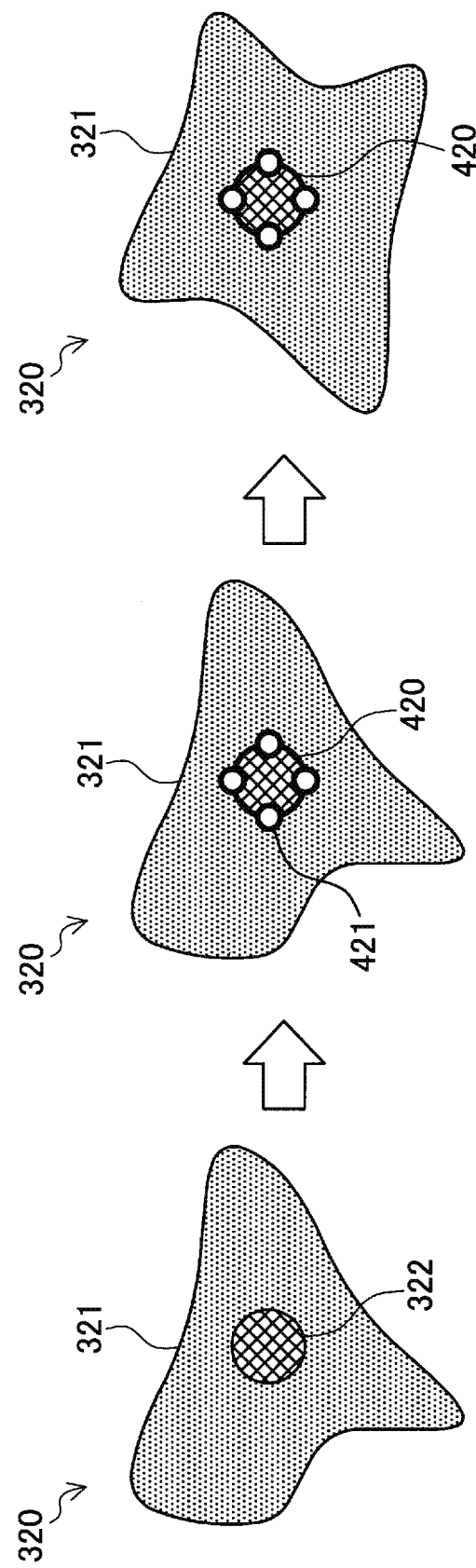

[Fig. 5]
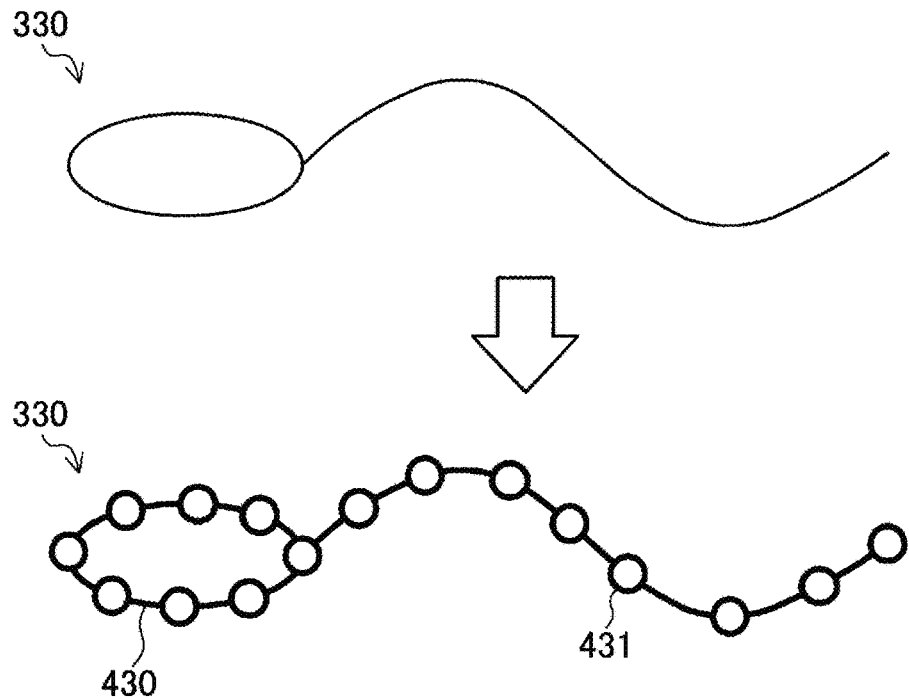
[Fig. 6]
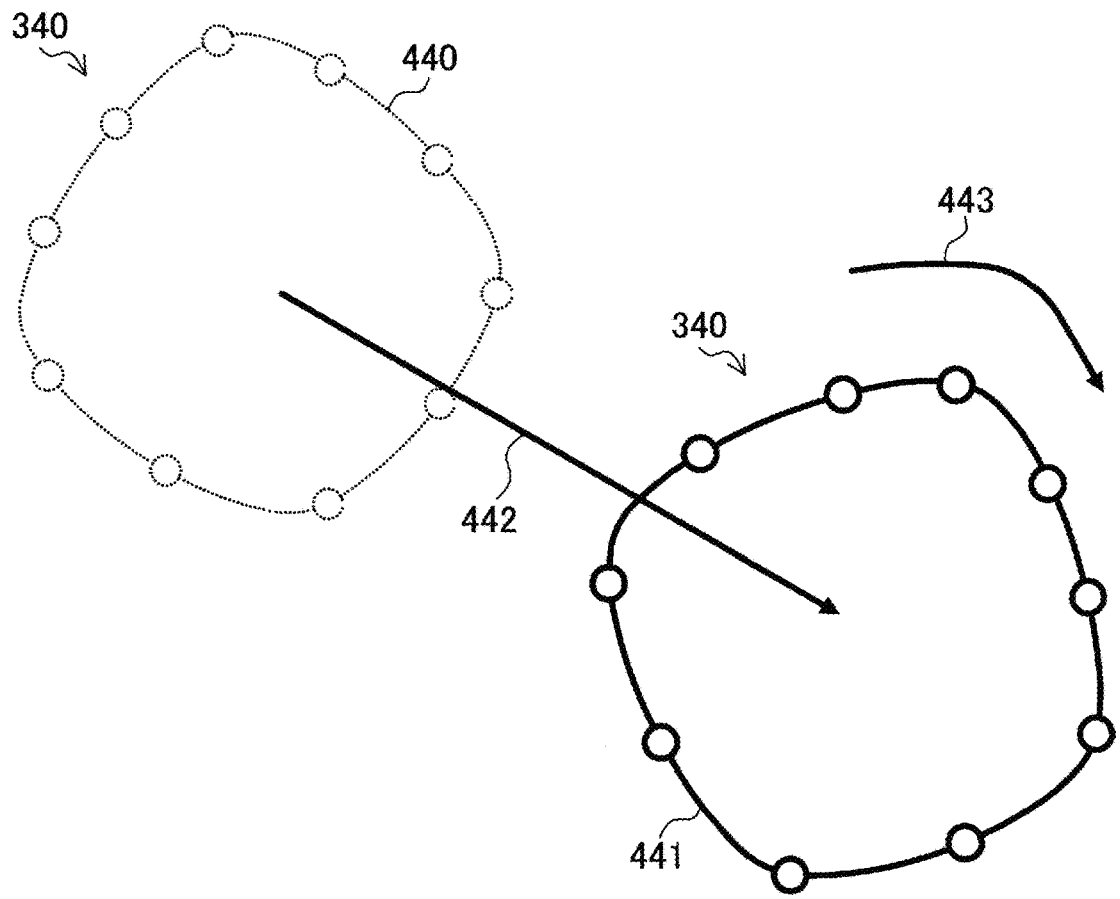

[Fig. 7]
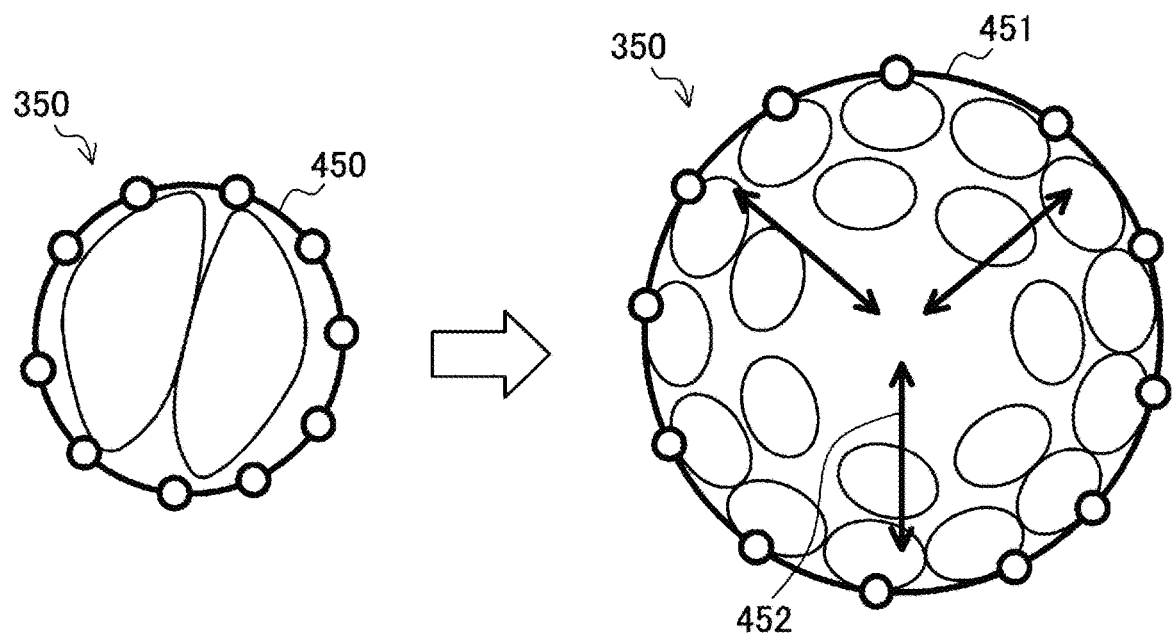

[Fig. 8]
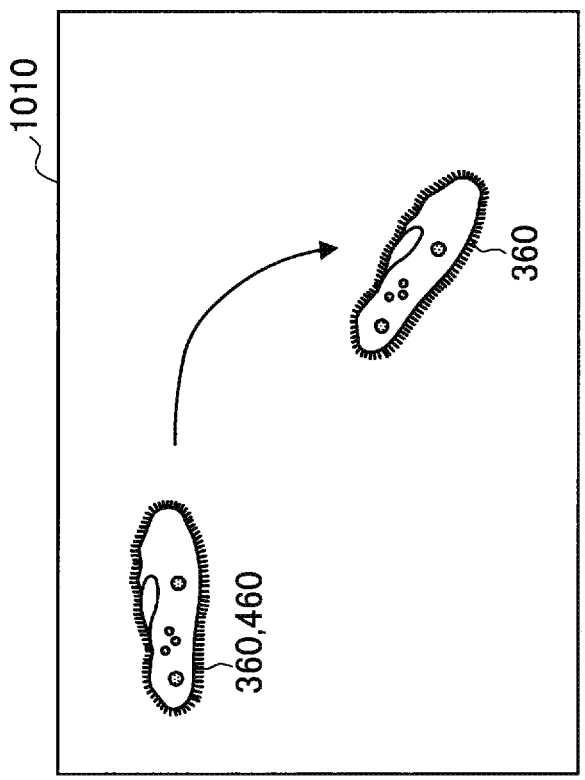
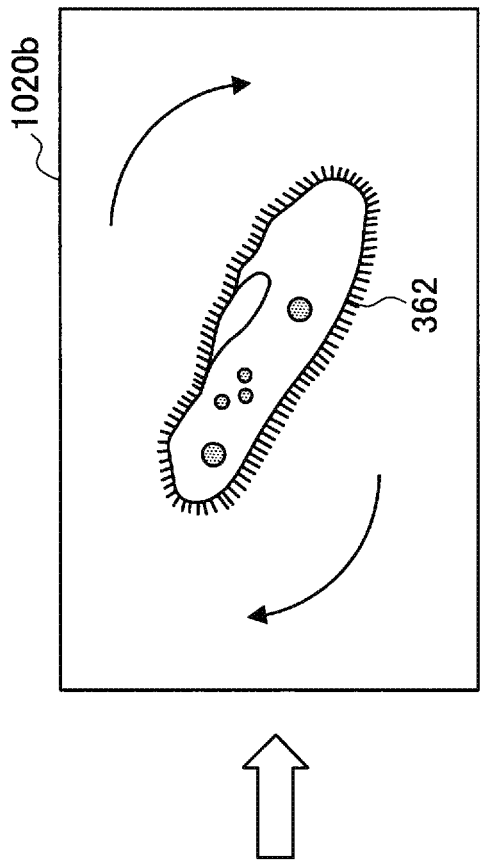
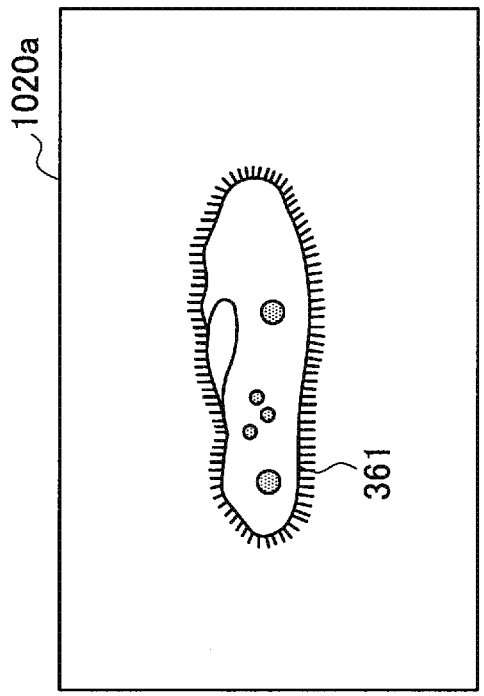

[Fig. 9]
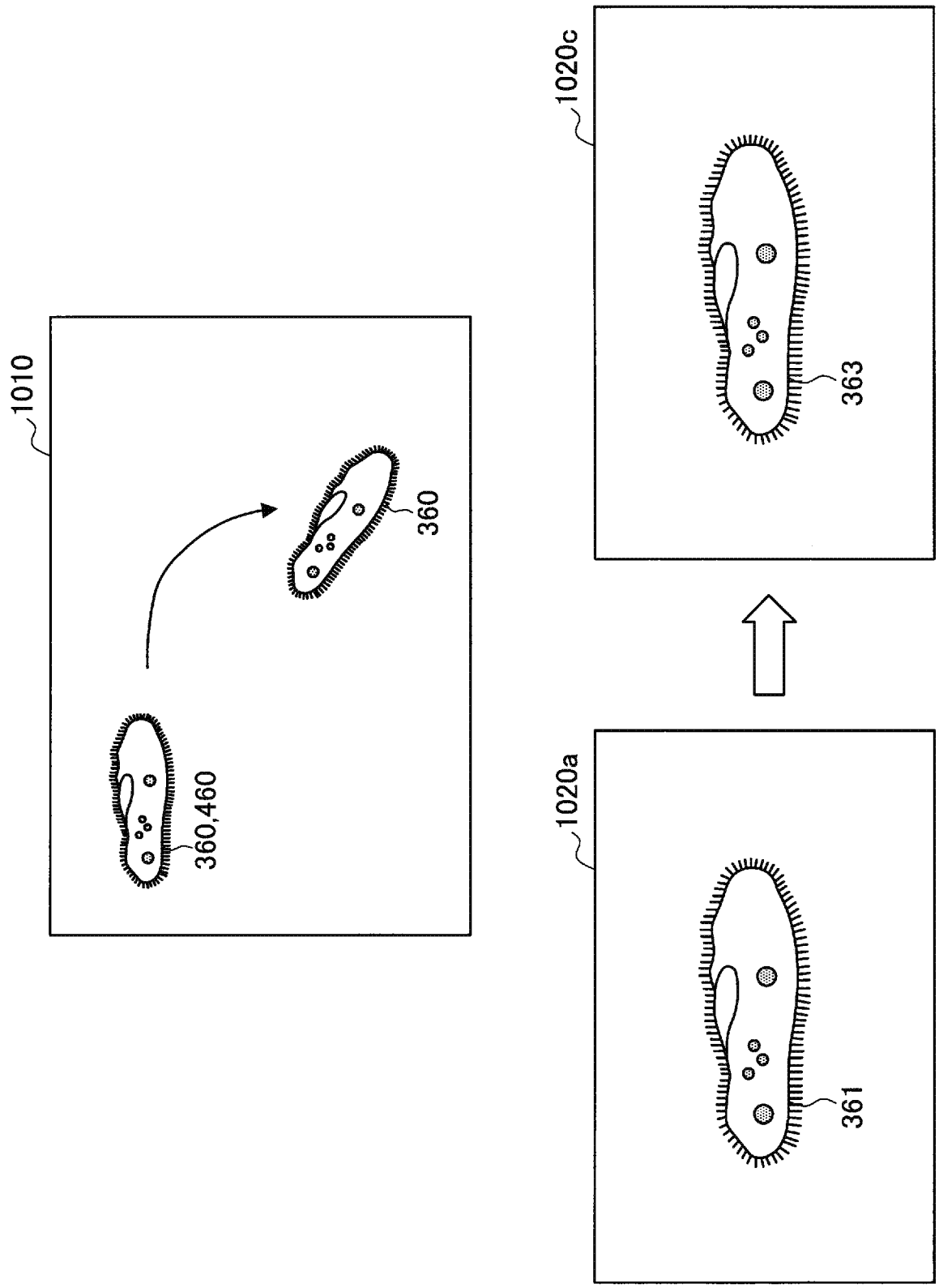

[Fig. 10]
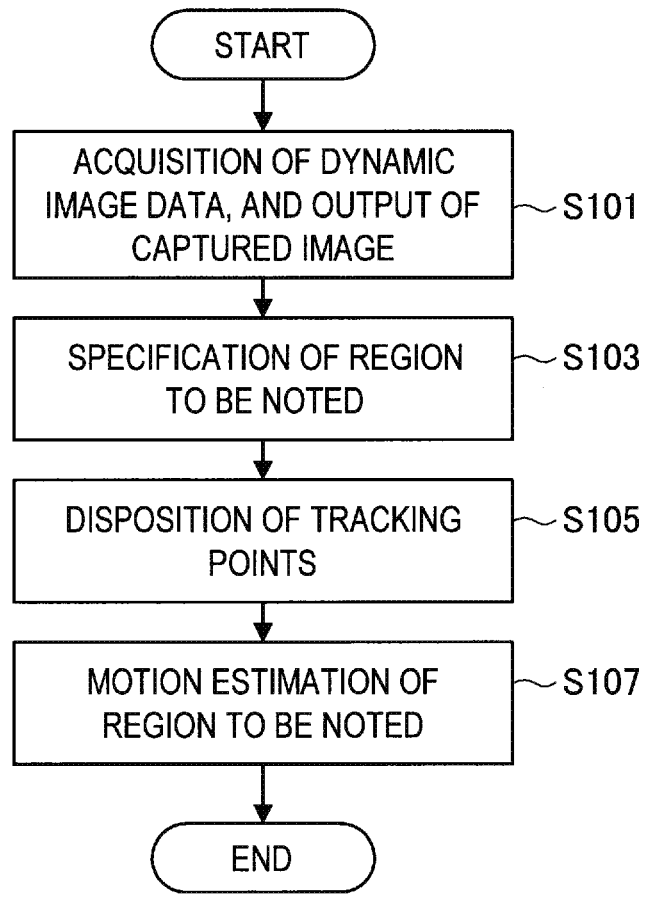

[Fig. 11]
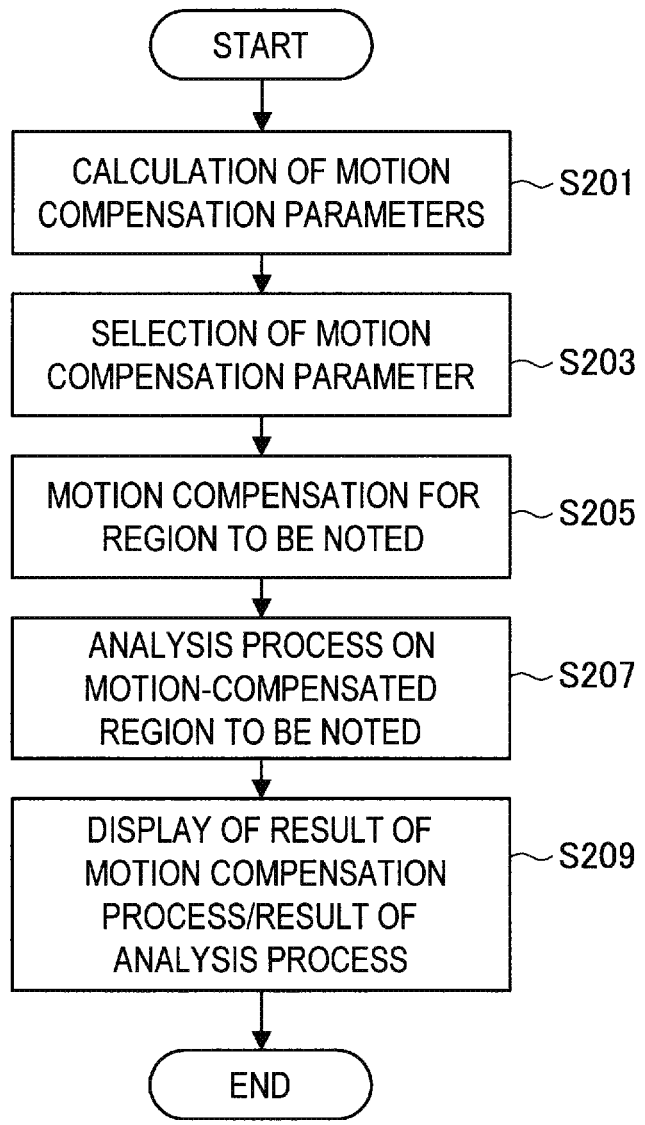

[Fig. 12]
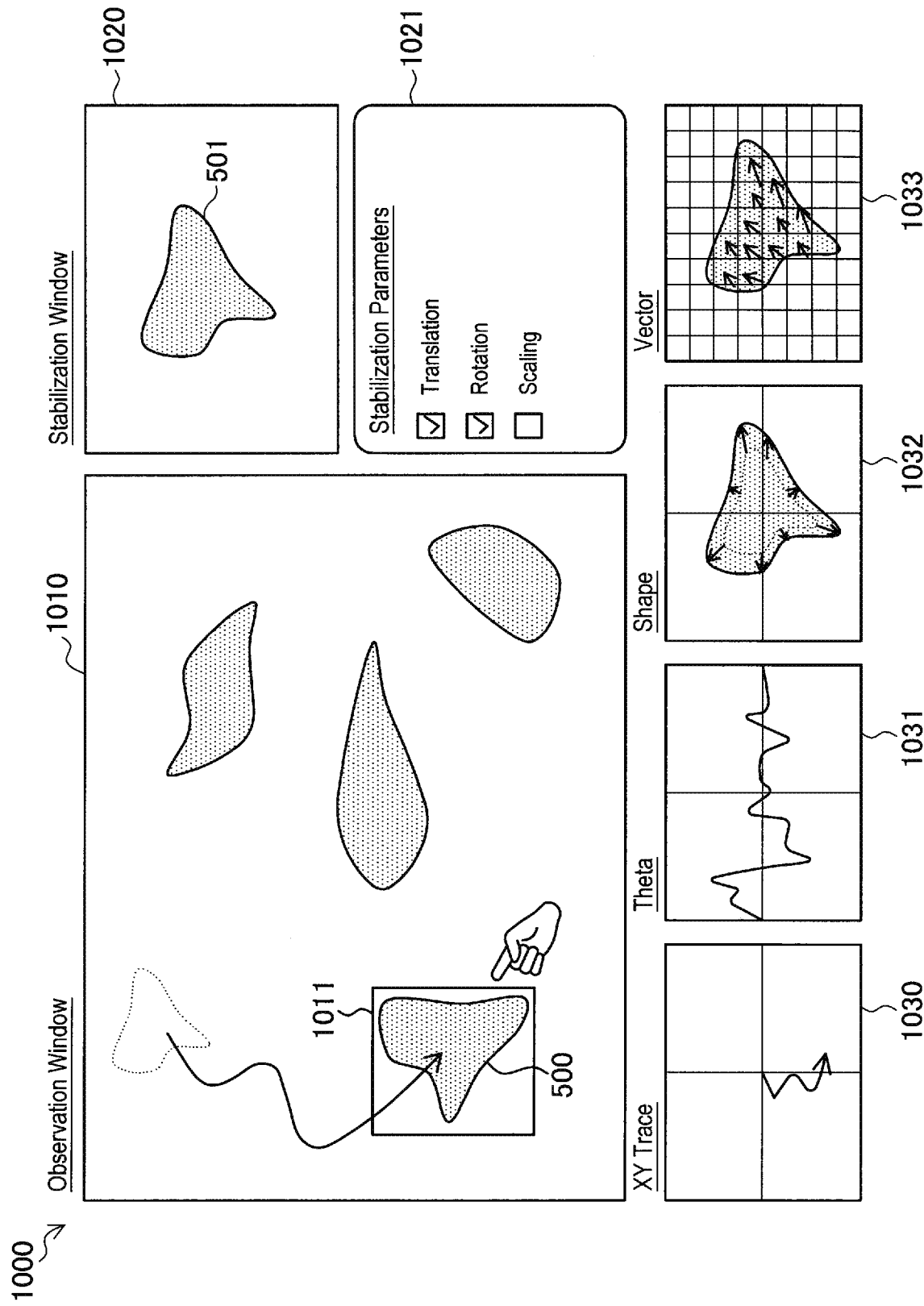

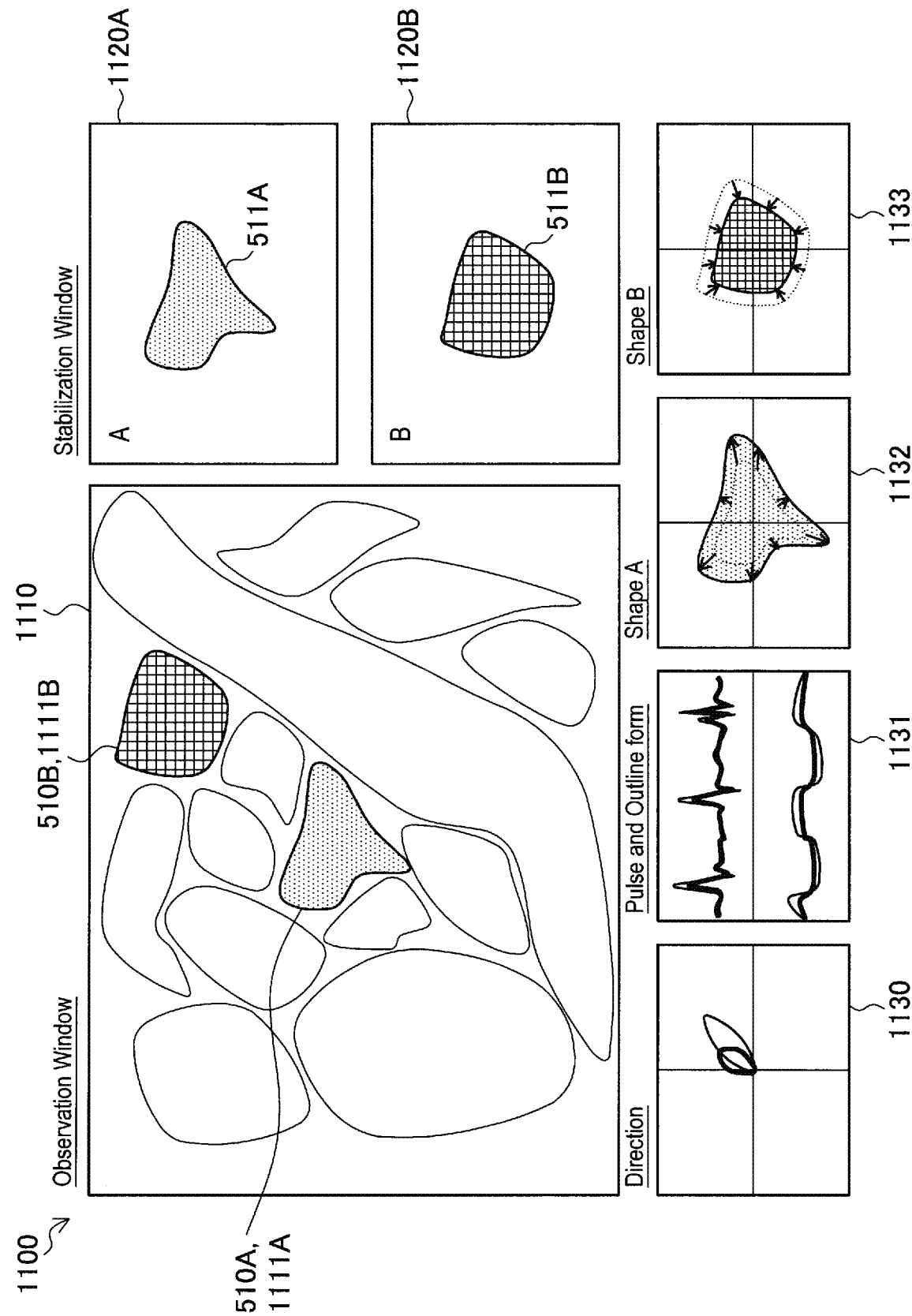
[Fig. 13]

[Fig. 14]
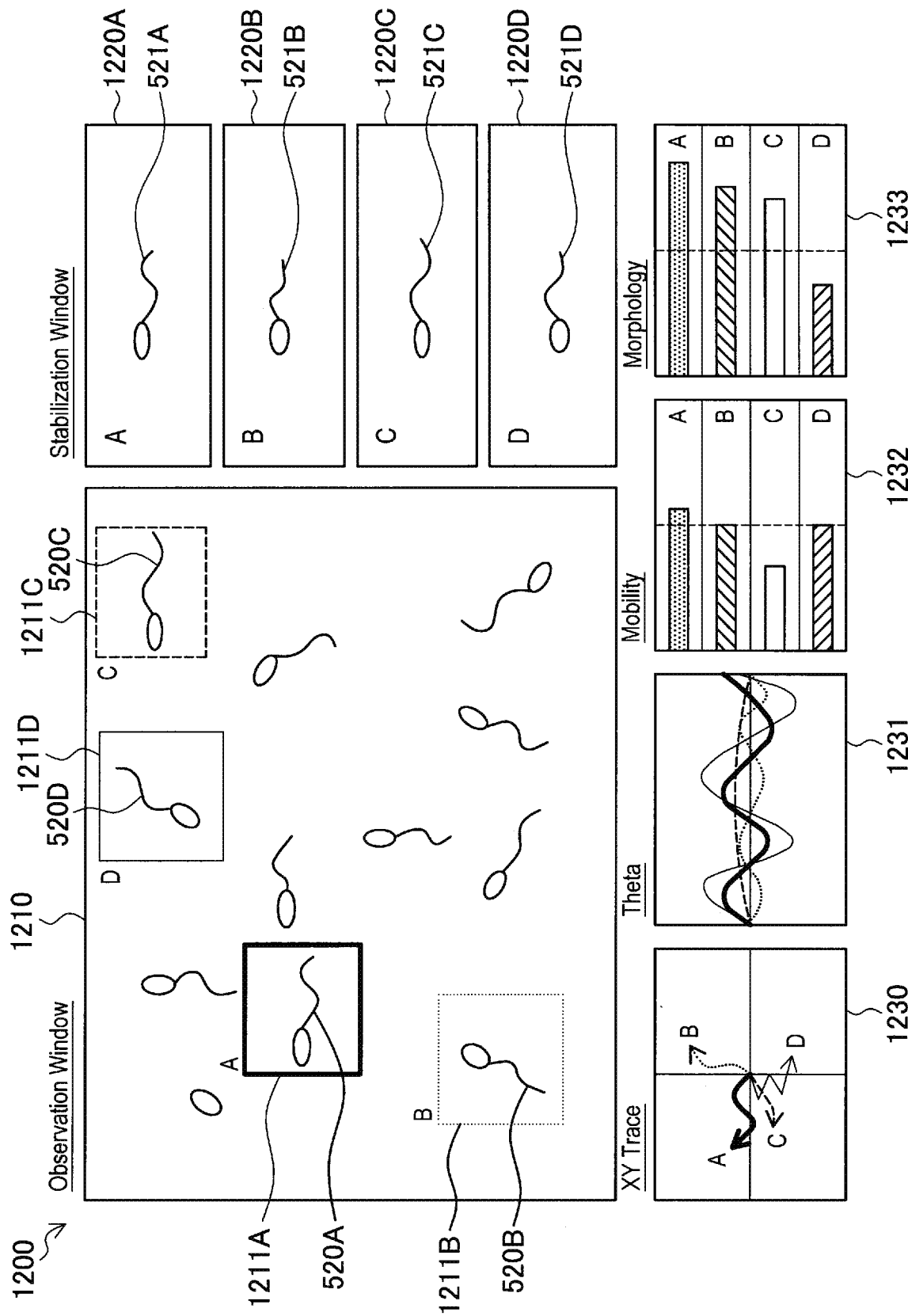

[Fig. 15]
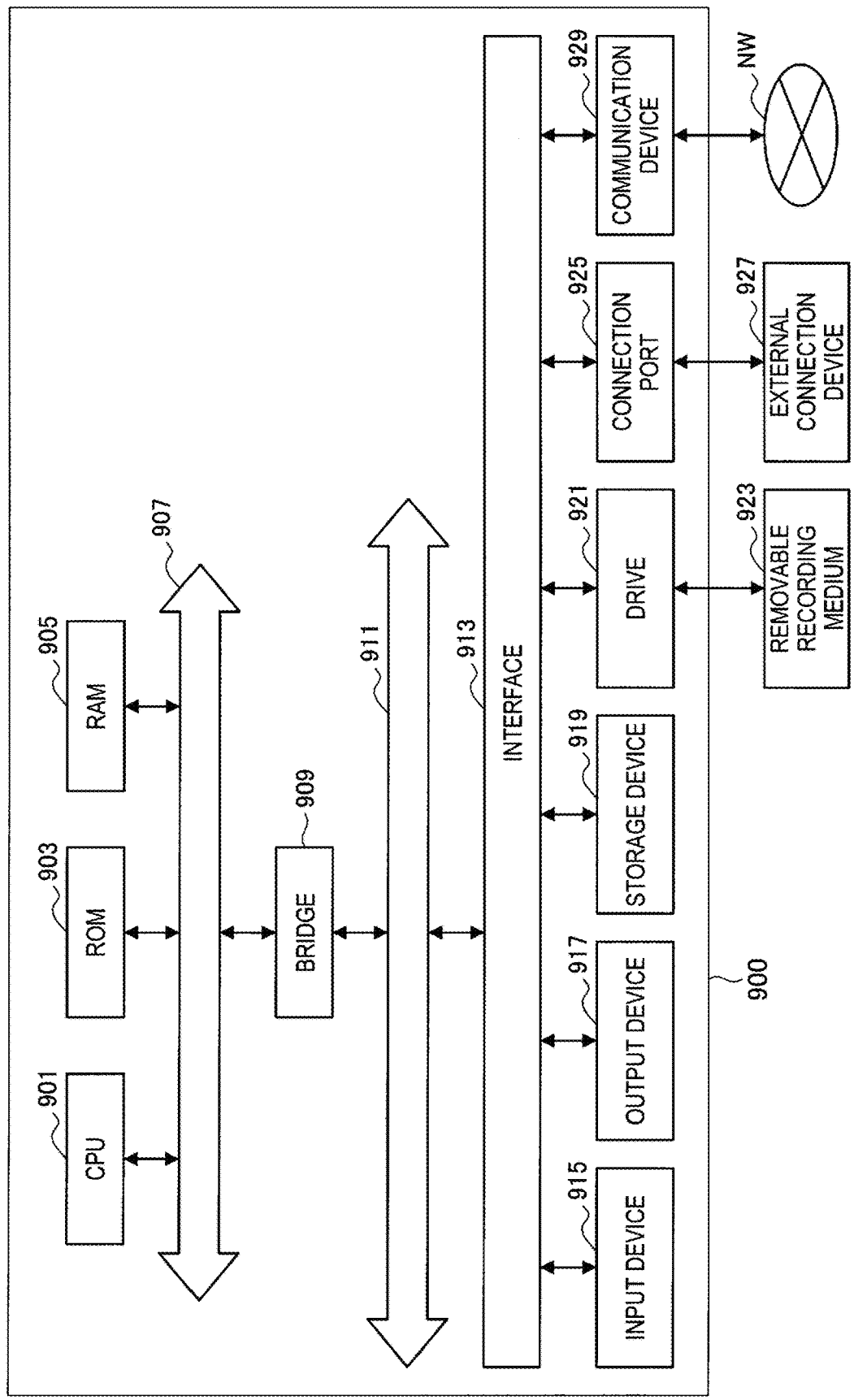

INFORMATION PROCESSING DEVICE, INFORMATION PROCESSING METHOD, PROGRAM, AND INFORMATION PROCESSING SYSTEM

CROSS REFERENCE TO RELATED APPLICATIONS

This Application is a national stage entry filed under 35 U.S.C. 371 of PCT Application Serial No. PCT/JP2016/082809, filed Nov. 4, 2016, titled "INFORMATION PROCESSING DEVICE, INFORMATION PROCESSING METHOD, PROGRAM, AND INFORMATION PROCESSING SYSTEM." PCT Application Serial No. PCT/JP2016/082809 claims priority to Japanese Priority Patent Application JP 2015-221330 filed Nov. 11, 2015, which is incorporated herein by reference in its entirety.

TECHNICAL FIELD

The present disclosure relates to an information processing device, an information processing method, a program, and an information processing system.

BACKGROUND ART

In the fields of medicine and life science, motions of many types of biological samples are observed, and changes in their forms are evaluated. Changes in forms of biological samples are motions that reflect their life activities or life states, and are closely related to evaluation of states and the like of the biological samples. Such a change in a form of a biological sample is often distorted by various motions such as autonomous locomotion of the biological sample, vibration of an observation device, or drifting of a culture, and thus there are few occasions on which only changes in forms of biological samples can be observed with no influence. Thus, identifying a change in a form of a biological sample from various motions of the biological sample with high accuracy is important for analyzing the change in its form exactly. Consequently, an image processing technology for identifying a change in a form of a biological sample from various motions carried out by the biological sample and for observing and analyzing the change in the form of the biological sample has been demanded.

For example, PTL 1 discloses a technology of estimating motions of consecutive frame images and stabilizing an image space using the result of the estimation and an initial frame image. With this technology, disturbances in a dynamic image caused by an external factor such as a shake in camera work can be corrected.

CITATION LIST

Patent Literature

PTL 1: JP 2005-102082A

SUMMARY

Technical Problem

However, the technology disclosed in PTL 1 mentioned above is for correcting disturbances of a dynamic image caused by movements of an imaging device imaging an image space. Thus, it is difficult in the technology disclosed in the above-mentioned document to catch only a change in a form of a biological sample from motions of the biological sample moving in the range of the same angle of view.

Therefore, the present disclosure proposes a novel and improved information processing device, information processing method, program, and information processing system that can analyze a change in a form of a biological sample more exactly.

Solution to Problem

According to an aspect of the present application, an information processing device is provided. The information processing device includes circuitry configured to set at least one region of an image of a biological sample and select a motion compensation parameter calculated based at least on a motion of the at least one region. The circuitry is further configured to control display of a result of performing a process on the at least one region using the selected motion compensation parameter.

According to an aspect of the present application, an information processing method performed by a processor is provided. The method includes setting at least one region of an image of a biological sample and selecting a motion compensation parameter calculated based at least on a motion of the at least one region. The method further includes controlling display of a result of performing a process on the at least one region using the selected motion compensation parameter.

According to an aspect of the present application, at least one computer-readable storage medium storing computer-executable instructions that, when executed, perform a method is provided. The method includes setting at least one region of an image of a biological sample and selecting a motion compensation parameter calculated based at least on a motion of the at least one region. The method further includes controlling display of a result of performing a process on the at least one region using the selected motion compensation parameter.

According to an aspect of the present application, an information processing system is provided. The information processing system includes an imaging device configured to generate an image of a biological sample. The information processing system further includes circuitry configured to set at least one region of an image of a biological sample and select a motion compensation parameter calculated based at least on a motion of the at least one region. The circuitry is further configured to control display of a result of performing a process on the at least one region using the selected motion compensation parameter.

Advantageous Effects of Invention

According to embodiments of the present disclosure described above, it is possible to analyze a change in a form of a biological sample more exactly.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 1 is a diagram showing an overview of a configuration of an information processing system according to an embodiment of the present disclosure.

FIG. 2 is a functional block diagram showing a functional configuration example of an information processing device according to the embodiment.

FIG. 3 is a diagram showing an example of a region-to-be-noted setting method of a setting unit for a fertilized egg.

FIG. 4 is a diagram showing an example of a region-to-be-noted setting method of the setting unit for a wandering cell.

FIG. 5 is a diagram showing an example of a region-to-be-noted setting method of the setting unit for a sperm.

FIG. 6 is a diagram for describing a translation component and a rotation component constituting a motion of a region to be noted.

FIG. 7 is a diagram for describing a scaling component constituting a motion of a region to be noted.

FIG. 8 is a diagram showing an example of a motion-compensated image when only a motion compensation parameter corresponding to a translation component is selected.

FIG. 9 is a diagram showing an example of a motion-compensated image when only motion compensation parameters corresponding to a translation component and a rotation component are selected.

FIG. 10 is a flowchart showing an example of a motion estimation process performed by the information processing device according to the embodiment.

FIG. 11 is a flowchart showing an example of a motion compensation process and an analysis process performed by the information processing device according to the embodiment.

FIG. 12 is a diagram showing a first application example of the information processing device according to the embodiment.

FIG. 13 is a diagram showing a second application example of the information processing device according to the embodiment.

FIG. 14 is a diagram showing a third application example of the information processing device according to the embodiment.

FIG. 15 is a block diagram showing a hardware configuration example of an information processing device according to an embodiment of the present disclosure.

DESCRIPTION OF EMBODIMENTS

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that description will be provided in the following order.

1. Overview of information processing system
2. Information processing device
2.1. Configuration example
2.2. Process example
2.3. Application example
2.4. Effect
3. Hardware configuration example
4. Conclusion

1. OVERVIEW OF INFORMATION PROCESSING SYSTEM

FIG. 1 is a diagram showing an overview of a configuration of an information processing system 1 according to an embodiment of the present disclosure. As shown in FIG. 1, the information processing system 1 is provided with an imaging device 10 and an information processing device 20. The imaging device 10 and the information processing device 20 are connected to each other via various types of wired or wireless networks.

(Imaging Device)

The imaging device 10 is a device which generates captured images (dynamic images). The imaging device 10 according to the present embodiment is realized by, for example, a digital camera. In addition, the imaging device 10 may be realized by any type of device having an imaging function, for example, a smartphone, a tablet, a game device, or a wearable device. The imaging device 10 images real spaces using various members, for example, an image sensor such as a charge coupled device (CCD) or a complementary metal oxide semiconductor (CMOS), a lens for controlling formation of a subject image in the image sensor, and the like. The image sensor and the various members realize the function of the imaging device 10 as an imaging unit. In addition, the imaging device 10 includes a communication device for transmitting and receiving captured images and the like to and from the information processing device 20. In the present embodiment, the imaging device 10 is provided above an imaging stage S to image a culture medium M in which a cell that is an observation target is cultured. Note that the cell is an example of a biological sample. In addition, the imaging device 10 generates dynamic image data by imaging the culture medium M at a specific frame rate. Note that the imaging device 10 may directly image the culture medium M (without involving another member), or may image the culture medium M via another member such as a microscope. In addition, although the frame rate is not particularly limited, it is desirable to set the frame rate according to the degree of a change of the observation target. Note that the imaging device 10 images a given imaging region including the culture medium M in order to accurately track a change of the observation target. Dynamic image data generated by the imaging device 10 is transmitted to the information processing device 20.

Note that, although the imaging device 10 is assumed to be a camera installed in an optical microscope or the like in the present embodiment, the present technology is not limited thereto. For example, the imaging device 10 may be an imaging device included in an electronic microscope using electron beams such as a scanning electron microscope (SEM) or a transmission electron microscope (TEM), or an imaging device included in a scanning probe microscope (SPM) that uses a probe such as an atomic force microscope (AFM) or a scanning tunneling microscope (STM). In this case, a dynamic image generated by the imaging device 10 is a dynamic image obtained by irradiating the observation target with electron beams in the case of an electronic microscope. In addition, when the imaging device 10 is an SPM, a dynamic image generated by the imaging device 10 is a dynamic image obtained by tracing an observation target using a probe. These dynamic images can also be analyzed by the information processing device 20 according to the present embodiment.

(Information Processing Device)

The information processing device 20 is a device having an image analyzing function. The information processing device 20 is realized by any type of device having an image analyzing function such as a personal computer (PC), a tablet, or a smartphone. The information processing device 20 includes a processing circuit and a communication device. For example, in the information processing device 20 according to the present embodiment, the communication device acquires a dynamic image from the imaging device 10, and the processing circuit estimates a motion of an observation target for the acquired dynamic image. In addition, the processing circuit calculates motion compensation parameters from the estimated motion of the observation target, and performs processes such as motion compensation and analysis of the observation target based on the motion compensation parameters. The results of the processes performed by the processing circuit of the information processing device 20 are output to a storage device, a display device, or the like provided inside or outside the information processing device 20. Note that the information processing device 20 may be realized by one or a plurality of information processing devices on a network. A functional configuration for realizing the respective functions of the information processing device 20 will be described below.

Note that, although the information processing system 1 is constituted with the imaging device 10 and the information processing device 20 in the present embodiment, the present technology is not limited thereto. For example, the imaging device 10 may perform the processes of the information processing device 20 (for example, a motion compensation process and an analysis process). In this case, the information processing system 1 can be realized by the imaging device having the motion compensation function and the analysis function.

In addition, an observation target of the information processing system 1 according to the present embodiment is mainly a biological sample. A biological sample is an organism which can be observed using an optical microscope or the like, for example, any of various types of cells, cell organelles or biological tissues, or living organisms such as micro-organisms or plankton. A biological sample in the present embodiment in particular is an organism that can move in the culture M on the imaging stage S of the imaging device 10. Such a biological sample will be referred to hereinafter as an observation target. Note that, although an observation target is a biological sample in the present embodiment, the present technology is not limited thereto. For example, an observation target may be a structure such as a living or non-living organism having a size in a scale from millimeters to nano-meters. More specifically, the observation target may be a compound, a membrane, a micro-particle, a nano-particle, or the like, and the information processing system 1 may be used to analyze crystal growth of the observation target or the like.

Here, a cell set as an observation target undergoes various phenomena such as growth, division, combination, deformation, or necrosis in a short period of time, unlike a normal subject such as a human, an animal, a plant, or a non-living structure. A cell shows a change in its form or motion (which will be collectively referred to as a change in a form) according to these various phenomena. Such changes in forms have previously been subjected to qualitative evaluation through visual observation by an observer. Changes in forms of biological samples are often distorted by autonomous locomotion of the biological samples, vibration of an observation device, or drifting of a culture. Thus, there are few occasions on which only a change in a form of a biological sample can be observed with no influence. That is, it is difficult to observe a change in a form of a biological sample through visual observation, which imposes an even bigger burden on an observer. In addition, even when it is attempted to analyze the uninfluenced motion of a biological sample, various kinds of motions other than a change in a form of the biological sample may be included in the analysis, and thus it is hard to obtain a reliable analysis result.

In order to observe and analyze such a change in a form of a cell exactly, it is requested to identify the change in the form from various motions that the biological sample makes. However, a cell can significantly change its position and form in a short period of time as described above. Thus, even if the technology disclosed in PTL 1 is used, for example, the technology merely corrects disturbances of a dynamic image caused by movements of an imaging device imaging an image space. Therefore, it is difficult to catch only a change in a form of a biological sample from motions of the biological sample moving in the range of the same angle of view.

Therefore, in the information processing system 1 according to the present embodiment, a region corresponding to an observation target (region to be noted) is set from one captured image constituting a dynamic image, a motion of the region to be noted is estimated, motion compensation parameters are calculated based on the estimated motion, and processes are performed on the region to be noted using the calculated motion compensation parameters. The processes performed on the region to be noted are, for example, a motion compensation process performed on the dynamic image including a region equivalent to the observation target using the motion compensation parameters, and an analysis process on the observation target corresponding to the region to be noted. With this technology, autonomous locomotion of a cell desired to be observed, a motion caused by vibration of the imaging device, or the like can be estimated, and such a motion other than a change in a form can be eliminated. That is, only a change in a form of a cell can be identified from various motions that a biological sample makes. Thus, even when the form of the cell changes in a time series manner, the change in the form of the cell can be exactly observed and analyzed.

The overview of the information processing system 1 according to an embodiment of the present disclosure has been described above. The information processing device 20 included in the information processing system 1 according to an embodiment of the present disclosure is realized in the following embodiment. A specific configuration example and a process example of the information processing device 20 will be described below.

2. INFORMATION PROCESSING DEVICE

Hereinafter, the information processing device 20 according to an embodiment of the present disclosure will be described with reference to FIGS. 2 to 13.

2.1. Configuration Example

FIG. 2 is a functional block diagram showing a functional configuration example of the information processing device 20 according to an embodiment of the present disclosure. As shown in FIG. 2, the information processing device 20 according to the present embodiment is provided with a communication unit 210, a setting unit 220, an estimation unit 230, a parameter calculation unit 240, a selection unit 250, a processing unit 260, and a display control unit 270. A function of the communication unit 210 is realized by the communication device provided in the information processing device 20. In addition, functions of the setting unit 220, the estimation unit 230, the parameter calculation unit 240, the selection unit 250, the processing unit 260, and the display control unit 270 are realized by the processing circuit such as a central processing unit (CPU) provided in the information processing device 20. Furthermore, information output by each function unit may be appropriately stored in a storage device that is not illustrated, or each function unit may acquire information from the storage device. Each function unit will be described below.

(Communication Unit)

The communication unit 210 is a communication section that the information processing device 20 has, and performs various types of communication with external devices in a wireless or a wired manner via a network (or directly). For example, the communication unit 210 performs communication with the imaging device 10. More specifically, the communication unit 210 acquires a dynamic image generated by the imaging device 10. In addition, the communication unit 210 may perform communication with devices other than the imaging device 10. For example, the communication unit 210 may transmit information regarding results of processes by the processing unit 260 to be described below to an external storage device or a display device.

Note that dynamic images that the communication unit 210 acquires include RGB dynamic images, grayscale dynamic images, or the like. When an acquired dynamic image is an RGB dynamic image, the information processing device 20 may convert the RGB dynamic image into a grayscale dynamic image. Accordingly, accuracy of various processes performed by the estimation unit 230 or the processing unit 260 to be described below can improve. In addition, a dynamic image that the communication unit 210 acquires may be a live-view image, a time-lapse image, or the like.

(Setting Unit)

The setting unit 220 sets at least one region to be noted from one captured image constituting a dynamic image that the communication unit 210 acquires. Note that a region to be noted refers to a region used to estimate a motion of an observation target in the present specification. This region to be noted may not necessarily coincide with a region corresponding to an observation target (for example, a biological sample such as a cell) in a dynamic image (which will be referred to hereinafter as an observation target region). A region to be noted may be set to, for example, a region formed with a closed curve corresponding to the contour of an observation target, or a region corresponding to an internal tissue of an observation target.

In addition, the region to be noted in the present specification may be a region expressed using, for example, an open curve (including a straight line), or may be a region surrounded by a closed curve (a curve whose starting point and ending point match). In addition, a plurality of closed regions or a region in the shape of 8 may be set as the region to be noted.

In addition, a region to be noted may be set through an operation of a user using the information processing device 20, or automatically detected from a dynamic image by the setting unit 220 using a technique such as image analysis. In the case of the latter, the setting unit 220 may detect an observation target region through image analysis. For example, the setting unit 220 may set a region to be noted according to a type of observation target.

In addition, the setting unit 220 may set one or a plurality of regions to be noted from one captured image. For example, when a plurality of observation targets are included in one captured image, the setting unit 220 may set regions to be noted for the respective observation targets for comparison of motions of these observation targets. Accordingly, the respective motions of the plurality of observation targets can be estimated and changes in their forms can be analyzed, and therefore the results of the analysis can be compared.

Note that the one captured image may be a captured image equivalent to a first frame of a dynamic image that the communication unit 210 acquires. By setting a region to be noted for the captured image of the first frame, the position of the region to be noted in the first frame can be a reference when, for example, motions of a region to be noted are analyzed in a dynamic image in a time series manner. Thus, the result of the analysis becomes more accurate than when a position of a region to be noted of an arbitrary captured image is set as a reference.

Here, when a region to be noted is set in one captured image, the setting unit 220 according to the present embodiment disposes a plurality of tracking points for the region to be noted. A tracking point mentioned in the present specification is a point disposed to correspond to a region to be noted set in a given captured image. In the present embodiment, for example, tracking points are disposed on a line or a contour defining a region to be noted with predetermined intervals. The estimation unit 230 to be described below estimates positions of the tracking points in another captured image captured at a different time point from the captured image used when the region to be noted is set. The estimation unit 230 can estimate a motion of the region to be noted based on movement positions of these tracking points. Furthermore, the estimation unit 230 may re-dispose the tracking points in proper positions for the region to be noted after the movement. Accordingly, estimation accuracy in the motion of the region to be noted can be heightened.

In addition, the number of tracking points disposed and disposition intervals thereof may be decided according to the type of observation target or the shape of a region to be noted. For example, when the shape of the region to be noted significantly changes, it is desirable to increase the number of the tracking points disposed and reduce their disposition intervals. Accordingly, even if the form of a cell significantly changes, the change in the form of the cell can be tracked with high accuracy. In addition, in order to reduce a load of calculation, it is desirable to reduce the number of the tracking points disposed and increase their disposition intervals.

Here, it is desirable for a region to be noted according to the present embodiment to be a region of an observation target region in a dynamic image that makes a relatively small change in its form. This is because, if a region making a relatively significant change in its form is set as a region to be noted, it is difficult to estimate with high accuracy the size of each of motion components (including a translation component, a rotation component, and a scaling component) according to the change in the form.

Table 1 shows region-to-be-noted setting methods recommended for respective biological samples used as observation targets.

TABLE 1

| Region-to-be-noted setting methods recommended for respective biological samples | | | |
|---|---|---|---|
| | Contour of cell membrane | Contour of cell nucleus | Outermost contour of object |
| Fertilized egg | Yes | Yes | Yes |
| Wandering cell | No | Yes | No |

TABLE 1-continued

Region-to-be-noted setting methods recommended for respective biological samples

|  | Contour of cell membrane | Contour of cell nucleus | Outermost contour of object |
|---|---|---|---|
| Cultured cell | No | Yes | No |
| Sperm | No | No | Yes |
| Blood corpuscle | No | No | Yes |

Because the cytoplasm and the inside of the cell nucleus of a fertilized egg make significant motions, for example, it is desirable to set a region equivalent to the contour of the cell nucleus or cell membrane (i.e., the outermost contour) as a region to be noted.

FIG. 3 is a diagram showing an example of a region-to-be-noted setting method of the setting unit 220 for a fertilized egg. Referring to FIG. 3, the fertilized egg 310 is composed of a cell membrane 311 and a divided embryo 312. Cleavage progresses in the inside of the fertilized egg 310 as time elapses. Thus, the fertilized egg 310 can make a significant change in its internal form. On the other hand, with regard to the cell membrane 311, although the cell membrane 311 becomes enormous in its size as time elapses, the shape of the cell membrane 311 does not significantly change. For this reason, it is desirable for the setting unit 220 to set a region equivalent to the cell membrane 311 as a region to be noted 410 and to dispose tracking points 411 on the contour indicating the cell membrane 311 as shown in FIG. 3. Accordingly, the change in the internal form of the fertilized egg 310 can be analyzed with high accuracy.

In addition, because the cell membrane of a wandering cell or a cultured cell makes relatively significant changes in its form, it is desirable to set regions equivalent to the contour of their cell nucleus as regions to be noted. FIG. 4 is a diagram showing an example of the region-to-be-noted setting method of the setting unit 220 for a wandering cell. Referring to FIG. 4, the wandering cell 320 is composed of a cell membrane 321 and a cell nucleus 322. The form of the cell membrane 321 of the wandering cell 320 significantly changes due to a wandering phenomenon. On the other hand, the form of the cell nucleus 322 is not changed much. For this reason, it is desirable for the setting unit 220 to set a region equivalent to the cell nucleus 322 as a region to be noted 420 and dispose tracking points 421 on the contour indicating the cell nucleus 322 as shown in FIG. 4. Accordingly, a motion or a change in the form of the wandering cell 320 can be analyzed with high accuracy, regardless of a change in the form of the cell membrane 321.

Furthermore, a nerve cell makes a significant change in the form of its axon as well, and thus it is desirable to set the contour of the cyton equivalent to a cell nucleus as a region to be noted.

In addition, because a sperm and a blood corpuscle make random changes in their form, it is desirable to set regions equivalent to their outermost contours as regions to be noted. FIG. 5 is a diagram showing an example of the region-to-be-noted setting method of the setting unit 220 for a sperm. While the sperm 330 has a form that does not significantly change, it locomotes at a relatively high speed while its head shakes (head shaking movement). Thus, it is desirable for the setting unit 220 to set a region equivalent to the sperm 330 as a region to be noted 430, and dispose tracking points 431 on the contour indicating the sperm 330 as shown in FIG. 5. Accordingly, even when the sperm 330 makes various motions at a high speed, the motions of the sperm 330 can be analyzed with high accuracy.

Furthermore, a region to be noted set by the setting unit 220 may be set according not only to the type of observation target but also to the type of evaluation or analysis on the observation target. For example, when an observation target is a cell, a region to be noted may be set according to whether a motion inside the cell or a motion of the entire cell is to be analyzed. When a motion inside the cell is an object to be analyzed, the setting unit 220 may set a region equivalent to the outermost contour of the cell as a region to be noted. Accordingly, the motion inside the cell can be observed and analyzed exactly, regardless of a motion of the outermost contour of the cell. On the other hand, when a motion of the entire cell is an object to be analyzed, the setting unit 220 may set a region equivalent to a biological tissue such as the cell nucleus inside the cell as a region to be noted. In this manner, by setting a region to be noted according to the type of observation target, or a technique of analysis or the type of evaluation, diverse changes in the form can be observed and analyzed more exactly.

Information with regard to the region to be noted by the setting unit 220 is output to the estimation unit 230.

(Estimation Unit)

The estimation unit 230 estimates a motion of the region to be noted in the dynamic image. For example, the estimation unit 230 estimates the motion of the region to be noted of one captured image constituting the dynamic image in another captured image of which a capturing time point is different from the one captured image. Specifically, the estimation unit 230 according to the present embodiment may first estimate motions of respective tracking points disposed in the region to be noted, and then estimate the motion of the region to be noted based on the estimated motions of the tracking points.

First, the estimation unit 230 according to the present embodiment estimates the motions of the tracking points disposed for the region to be noted set by the setting unit 220, and thereby estimates the motion of the region to be noted. Specifically, the estimation unit 230 estimates positions of the tracking points that have been disposed in one captured image in another captured image of which the capturing time point is different from the one captured image. The other captured image may be a captured image of any frame among a few frames before and after the frame of the one captured image. The estimation unit 230 estimates the motions of the tracking points in the dynamic image by performing a process for estimating positions of the tracking points in another captured image for respective captured images constituting the dynamic image.

The estimation unit 230 may estimate positions of the tracking points based on, for example, a motion vector calculated by comparing a captured image to another captured image. This motion vector may be a motion vector calculated for each tracking point. The motion vector may be calculated using a technique such as block matching, or a gradient method. In the present specification, the estimation unit 230 is described as estimating the motion vector using block matching.

For example, with regard to a tracking region in a predetermined size including tracking points, the estimation unit 230 may estimate positions of the tracking points in the other captured image by detecting a region of which information of pixels included in the tracking region of the captured image matches that of the other captured image from a predetermined search range of the other captured image. In this case, a size of the tracking region and the search range may be decided according to an imaging condition (for example, an imaging magnification) of the imaging device 10, the type of the observation target, the type of analysis performed on the observation target. When a movement of the observation target is large, for example, the tracking region or the search range may be set to be larger. Accordingly, accuracy in estimation of tracking points by the estimation unit 230 can be enhanced. In addition, when there are a number of tracking points for a region to be noted, the tracking region or the search range may be adjusted to be small in order to reduce a load of calculation.

In addition, the estimation unit 230 may estimate a position of a tracking point in the other captured image generated at an imaging time point decided based on information of the observation target. When a change in the morphology of an observation target of which a speed of the change in the morphology is slow is tracked, for example, a difference in captured images between a plurality of consecutive frames generated by the imaging device 10 is small. For this reason, when a change in the shape of an observation target of which a speed of the change in the shape is slow is tracked, the estimation unit 230 may perform an estimation process with a captured image a number of frames before or after the frame of the captured image as the other captured image. To be more specific, the estimation unit 230 may perform an estimation process with a captured image a number frames after the captured image as the other captured image. The frame interval between the captured image and the other captured image enables the data amount of the captured image that is subject to a tracking process to be reduced. Accordingly, it is possible to reduce a load of calculation and track a change in the morphology of the observation target over a long period of time. The frame interval can be appropriately set according to the type, a state, or the like of the observation target.

Next, the estimation unit 230 according to the present embodiment estimates the motion of the region to be noted from the motions of the tracking points. More specifically, the estimation unit 230 estimates the motion of the region to be noted from a group of motion vectors composed of motion vectors of the tracking points.

For example, the estimation unit 230 may estimate the motion of the region to be noted from the group of motion vectors using a coordinate transformation formula such as an affine transformation formula or a Helmert transformation formula. The motion of the region to be noted estimated using such a coordinate transformation formula refers to the size of at least one motion component constituting the motion. Motion components in the present embodiment include a translation component, a rotation component, and a scaling component. These motion components are expressed with transformation parameters to be described below.

Each of the motion components will be described. FIG. 6 is a diagram for describing a translation component and a rotation component constituting a motion of a region to be noted. Referring to FIG. 6, a region to be noted 440 corresponding to an observation target region 340 is assumed to move to a region to be noted 441. Components constituting the movement from this region to be noted 440 to the region to be noted 441 include a translation component 442 and a rotation component 443. Note that the translation component 442 according to the present embodiment is broken up into a translation component in the x direction and a translation component in the y direction in a planar coordinate system.

FIG. 7 is a diagram for describing a scaling component constituting a motion of a region to be noted. Referring to FIG. 7, a region to be noted 450 corresponding to an observation target region 350 is assumed to move to (expand into) a region to be noted 451 due to a motion of the observation target region 350. Components constituting the movement from this region to be noted 450 to the region to be noted 451 include a scaling component 452. A motion of a region to be noted is constituted by a translation component, a rotation component, and a scaling component as described above. In order to extract a motion of a region to be noted, the motion of the region to be noted has to be broken up into these components. The technique of a coordinate transformation is used to break it up into motion components of a region to be noted in the present embodiment.

As one example of the coordinate transformation formulae, first, an affine transformation formula will be described. An affine transformation is a coordinate transformation in which translational movement and a linear transformation (rotation, scaling, and shear strain) are combined. If the original coordinates of a tracking point are set to (x, y) and the coordinates of the tracking point after an affine transformation are set to (x', y'), the affine transformation formula is expressed as the following formulae (1) and (2). $a_0$ to $a_2$ and $b_0$ to $b_2$ of each formula are affine parameters, which are an example of the above-mentioned transformation parameters.

[Math.1]

$$x' = a_0 + a_1 x + a_2 y \qquad (1)$$

$$y' = b_0 + b_1 x + b_2 y \qquad (2)$$

Here, when the imaging device 10 according to the present embodiment is not a scanning-type imaging device, shear strain hardly occurs in a region to be noted, and thus shear strain components that are not related to the motion components can be eliminated. Thus, in the present embodiment, a Helmert transformation formula in which linear transformation due to shear strain is not considered may be used in place of an affine transformation formula. A Helmert transformation formula is expressed as the following formulae (3) and (4) based on the affine transformation formulae. In this case, (x', y') represents the coordinates of the tracking point after a Helmert transformation.

[Math.2]

$$x' = a_0 + \lambda \cos\theta \cdot x - \lambda \sin\theta \cdot y \qquad (3)$$

$$y' = b_0 + \lambda \cos\theta \cdot x + \lambda \cos\theta \cdot y \qquad (4)$$

In the above-described formulae (3) and (4), $a_0$ represents the size of a translation component in the x direction, $b_0$ represents the size of the translation component in the y direction, θ represents a rotation angle of a rotation component, and λ represents a scaling rate of a scaling component. That is, the transformation parameters $a_0$, $b_0$, θ, and λ represent the sizes of the motion components.

Here, if the coordinates of a tracking point after a movement are set to (u, v), there is an error e between the coordinates of the tracking point after the movement (u, v) and the coordinates of the tracking point after a Helmert transformation (x', y'). The error e is expressed as the following formula (5).

[Math. 3]

$$e = \frac{}{\sqrt{\{u-(a_0+\lambda\cos\theta\cdot x-\lambda\sin\theta\cdot y)\}^2+\{v-(b_0+\lambda\sin\theta\cdot x+\lambda\cos\theta\cdot y)\}^2}} \quad (5)$$

When N tracking points (1, . . . , n, . . . , N) are disposed for one region to be noted, the estimation unit 230 calculates $a_0$, $b_0$, θ, and λ so that the error $e_n$ has a minimum value for each tracking point. These calculated parameters represent the size of a motion in regard to the translation component, the rotation component, and the scaling component of the region to be noted. Note that, in order to calculate parameters of the respective motion components, for example, a known optimization technique such as a least squares method may be used.

Note that, although the size of the motion in regard to the motion components of the region to be noted is calculated using the Helmert transformation formula in the above-described example, the present technology is not limited thereto. For example, when the imaging device 10 is a scanning-type imaging device, the estimation unit 230 may calculate the size of a motion for the respective motion components of a region to be noted using the affine transformation formula. In this case, a strain value of shear strain is calculated, in addition to the size of the motion in regard to the translation component, the rotation component, and the scaling component. This strain value is not a component resulting from the motion of the observation target corresponding to the region to be noted, but can be used for a motion compensation process to be described below.

In addition, the estimation unit 230 may not estimate the sizes of all motion components, and for example, may estimate only the size of one motion component. Specifically, the estimation unit 230 may estimate only sizes of the translation component and the rotation component from the above-described coordinate transformation formulae.

In addition, although the estimation unit 230 is described as estimating the motion of the region to be noted by estimating the motions of the tracking points disposed by the setting unit 220 in the above-described example, the present technology is not limited thereto. For example, the estimation unit 230 may estimate a motion of a region to be noted by calculating a motion vector of each pixel included inside or outside the region to be noted. The estimation unit 230 may estimate a motion of a region to be noted by using, for example, an optical flow technique. In this case, the size of each motion component constituting a motion of a region to be noted may be calculated based on motion vectors of pixels estimated through optical flow.

The estimation unit 230 estimates the motion of the region to be noted for each captured image constituting the dynamic image. Then, the estimation unit 230 outputs information regarding the estimated motion of the region to be noted to the parameter calculation unit 240.

(Parameter Calculation Unit)

The parameter calculation unit 240 calculates motion compensation parameters based on the motion of the region to be noted. Specifically, the parameter calculation unit 240 may calculate the motion compensation parameters corresponding to the motion components based on the sizes of the motion components constituting the motion of the region to be noted estimated by the estimation unit 230.

A motion compensation parameter is, in the present specification, a parameter calculated based on a motion from a region to be noted in one captured image constituting a dynamic image to a region to be noted of another captured image captured at a different time point from the one captured image. This motion compensation parameter serves as a parameter of the processing unit 260 to be described below to perform motion compensation for an image in which a region to be noted is included.

The parameter calculation unit 240 calculates the motion compensation parameters by adding the sizes of the estimated motion of the region to be noted from the one captured image to the other captured image included in the dynamic image. For example, if a motion compensation parameter corresponding to the translation component in the x direction is set to A, A is the integrated value of the sizes $a_0$ of the translation component of the estimated motion of the region to be noted in the x direction from the one captured image to the other captured image. In addition, if a motion compensation parameter corresponding to the translation component in the y direction is set to B, a motion compensation parameter corresponding to the rotation component is set to Θ, and a motion compensation parameter corresponding to the scaling component is set to Λ, A, B, Θ, and Λ are expressed as shown in the following formulae (6) to (9). Here, m represents an m-th image frame of the dynamic image.

[Math.4]

$$A = \Sigma a_{0m} \quad (6)$$

$$B = \Sigma b_{0m} \quad (7)$$

$$\Theta = \Sigma \theta_m \quad (8)$$

$$\Lambda = \Sigma \lambda_m \quad (9)$$

The parameter calculation unit 240 may calculate motion compensation parameters corresponding to respective motion components, or calculate a motion compensation parameter corresponding only to a motion component selected by the selection unit 250 to be described below. For example, when performing a motion compensation process on the translation component and the rotation component of a region to be noted is selected in advance, the parameter calculation unit 240 may calculate only the motion compensation parameter A of the translation component in the x direction, the motion compensation parameter B of the translation component in the y direction, and the motion compensation parameter Θ of the rotation component. In addition, the parameter calculation unit 240 may calculate a motion compensation parameter only for the size of a motion component estimated by the estimation unit 230. When only sizes of the translation component and the rotation component are estimated by the estimation unit 230, for example, the parameter calculation unit 240 may only calculate the motion compensation parameters corresponding to the translation component and the rotation component.

The parameter calculation unit 240 outputs information with regard to the motion compensation parameters to the processing unit 260.

(Selection Unit)

The selection unit 250 selects a motion compensation parameter used in various processes performed by the processing unit 260 to be described below. A motion compensation parameter selected by the selection unit 250 refers to a motion compensation parameter corresponding to each motion component as described above. When motion compensation is performed by the processing unit 260 with regard to the translation component and the rotation component of a motion of a region to be noted, for example, the selection unit 250 selects the motion compensation parameter A of the translation component in the x direction, the motion compensation parameter B of the translation component in the y direction, and the motion compensation parameter Θ of the rotation component, and outputs information regarding the selected motion compensation parameters to the processing unit 260. Accordingly, the processing unit 260 can perform a motion compensation process with regard only to the translation component and the rotation component of the motion of the region to be noted.

The selection unit 250 selects at least one motion compensation parameter from a plurality of motion compensation parameters. The selection unit 250 according to the present embodiment may select, for example, the following combinations of motion compensation parameters.

(a) Motion compensation parameters corresponding to the translation component (A and B)

(b) Motion compensation parameters corresponding to the translation component and the rotation component (A, B, and Θ)

(c) Motion compensation parameters corresponding to the translation component, the rotation component, and the scaling component (A, B, Θ, and Λ).

When the selection unit 250 selects (a) above, the motion compensation process for a dynamic image related to an observation target region performed by the processing unit 260 which will be described below is performed with regard only to the translation component. That is, the observation target region can change in a rotation direction and an scaling direction, rather than changing in a translation direction in a motion-compensated image after the motion compensation process. In other words, the observation target region can exhibit a rotational movement or a scaling movement at the same position. In addition, when the selection unit 250 selects (b) above, the motion compensation process for the dynamic image related to the observation target region is performed with regard to the translation component and the rotation component. That is, the region to be noted can change in a scaling direction, rather than changing in a translation direction and a rotation direction in a motion-compensated image. In other words, the observation target region can exhibit a scaling movement at the same position. In addition, when the selection unit 250 selects (c) above, the motion compensation process for the dynamic image related to the observation target region is performed with regard to all the motion components. That is, the observation target region looks as if it is making no movement in the motion-compensated image. Note that a combination of the motion compensation parameters selected by the selection unit 250 is not limited to the examples of (a) to (c) described above.

Characteristics of a motion-compensated image resulting from selection of the motion compensation parameters by the selection unit 250 will be further described. FIG. 8 is a diagram showing an example of a motion-compensated image when only a motion compensation parameter corresponding to the translation component is selected. Referring to FIG. 8, an observation target region 360 is moving in a translation and rotation direction in a dynamic image captured by the imaging device 10 and displayed on an original dynamic image display screen 1010. Note that a closed curve is assumed to be disposed to specify a region to be noted 460 on the outermost profile of the observation target region 360. In this case, the selection unit 250 is assumed to select only the motion compensation parameter corresponding to the translation component. A motion-compensated image 1020a includes an observation target region 361 before movement, and a motion-compensated image 1020b includes an observation target region 362 after movement. When the processing unit 260 performs a motion compensation process, the observation target region 362 in the motion-compensated image 1020b rotates clockwise at the same position as that of the observation target region 361 of the motion-compensated image 1020a. That is, when only the motion compensation parameter corresponding to the translation component is selected, movement of the observation target in the rotation direction can be observed and analyzed. For example, a speed of rotation movement, and the center position of the rotation movement of the observation target can be observed and analyzed.

FIG. 9 is a diagram showing an example of a motion-compensated image when only the motion compensation parameters corresponding to the translation component and the rotation component are selected. Referring to FIG. 9, the observation target region 360 moves in translation and rotation directions in the dynamic image captured by the imaging device 10 and displayed on the original dynamic image display screen 1010 as in FIG. 8. Note that the closed curve is assumed to be disposed to specify the region to be noted 460 on the outermost profile of the observation target region 360. In this case, the selection unit 250 is assumed to select the motion compensation parameters corresponding to the translation component and the rotation component. The motion-compensated image 1020a includes the observation target region 361 before movement, and a motion-compensated image 1020c includes an observation target region 363 after movement. When the processing unit 260 performs a motion compensation process, the position and the orientation of the observation target region 363 in the motion-compensated image 1020c are the same as those of the observation target region 361 in the motion-compensated image 1020a. That is, when the motion compensation parameters corresponding to the translation component and the rotation component are selected, the observation target can be observed and analyzed in a state in which a motion of the observation target seems to stop. For example, an internal motion of the observation target can be observed and analyzed exactly.

As described above, a change in the form of the observation target can be observed according to a purpose of observation when the selection unit 250 selects a motion compensation parameter. Note that the selection of a motion compensation parameter by the selection unit 250 may be performed based at least on any of the type of observation target, or an analysis method for an observation target. That is, the selection unit 250 may select at least one motion compensation parameter based at least on the type of observation target, or a technique of analysis for the observation target. In some embodiments, a type of the observation target may be selected by analyzing an image of the observation target to identify one or more characteristics of the observation target. The one or more characteristics of the observation target may be used to determine the type of the observation target. A characteristic of the observation target may include size, shape, movement or any suitable characteristic of the observation target. In some embodiments, the type of the observation target may be determined automatically based on one or more characteristics of the observation target. A type of the observation target may be selected based on a characteristic (e.g., composition, scale) of the image of the observation target. The characteristic of the image of the observation target may be used to automatically determine the type of the observation target. In other embodiments, a user may provide user input identifying a type of the observation target in an image. Selection of at least one motion compensation parameter may be based on the type of the observation target identified by the user input, which may be considered as manual selection of the type of observation target. Examples of selecting a motion compensation parameter will be introduced below.

(1) Cases in which only the motion compensation parameter corresponding to the translation component is to be selected The selection unit 250 may select, for example, the motion compensation parameter corresponding to the translation component in the following cases.

When it is desired to analyze an observation target exhibiting a locomotive phenomenon in which its length of locomotion is considerable (for example, when it is desired to analyze a change in an internal form of a wandering cell)

When it is desired to eliminate influence of an autonomous motion of an observation target caused by periodic movement (for example, when it is desired to extract only periodic scaling movement of a myocardial cell)

When it is desired to analyze autonomous rotation movement of an observation target (for example, when it is desired to analyze head-shaking movement of a sperm)

When it is desired to correct blur caused by a drift phenomenon (for example, when it is desired to correct blur caused by drifting of a blood vessel image resulting from pulsation of a living organism)

(2) Cases in which the motion compensation parameters corresponding to the translation component and the rotation component are to be selected The selection unit 250 may select, for example, the motion compensation parameters corresponding to the translation component and the rotation component in the following cases.

When it is desired to analyze a change in a motion made inside a cell (for example, when it is desired to analyze a cleavage phenomenon of a fertilized egg or an internal motion of a blood cell)

When it is desired to analyze a change in the form of a cell (for example, when it is desired to analyze a change in the form of a cytoplasm included in a unicellular organism)

When there is influence caused by an external factor such as vibration of the imaging device 10 in a case in which cells or living organisms distributed in a container at a low density are observed When it is desired to quantitatively analyze a shape of a cell or a living organism (for example, when it is desired to compare sizes or shapes of sperm)

By selecting a motion compensation parameter based on an analysis process to be executed by the processing unit 260 as described above, it is possible to perform optimum selection even if a user selects no motion compensation parameter.

Information regarding selection of a motion compensation parameter by the selection unit 250 is output to the processing unit 260.

In addition, the selection unit 250 may select a motion compensation parameter to be calculated by the parameter calculation unit 240. Specifically, the selection unit 250 may select a motion component of a motion compensation parameter to be calculated by the parameter calculation unit 240 among the motion compensation parameters. In this case, information regarding the selection of the motion compensation parameter by the selection unit 250 is output to the parameter calculation unit 240. The parameter calculation unit 240 only calculates the motion compensation parameter corresponding to the motion component selected by the selection unit 250. Accordingly, a load imposed on the parameter calculation unit 240 to calculate the motion compensation parameters can be reduced.

(Processing Unit)

The processing unit 260 performs a process on the region to be noted using the motion compensation parameter calculated by the parameter calculation unit 240. The processing unit 260 according to the present embodiment further includes a motion compensation unit 261 and an analysis unit 262 as function units which perform specific processes on the dynamic image. The function units will be described below.

(Motion Compensation Unit)

The motion compensation unit 261 performs a motion compensation process on the dynamic image including the observation target region corresponding to at least one region to be noted using the motion compensation parameters. The motion compensation process referred to in the present specification is a process of performing a coordinate transformation on all or a part of another captured image that is different from one captured image with a coordinate transformation formula using the motion compensation parameters. An image obtained from the motion compensation process is a motion-compensated image. That is, the motion compensation unit 261 generates a motion-compensated image through the motion compensation process.

A motion-compensated image that the motion compensation unit 261 obtains may be, for example, a motion-compensated image obtained by performing the motion compensation process on a captured image constituting a dynamic image. In this case, when the display control unit 270 to be described below causes the motion-compensated image to be displayed on a display unit that is not illustrated, for example, only a region including the region to be noted may be displayed. Specifically, the display control unit 270 may extract only an observation target region corresponding to a region to be noted from a captured image that has undergone the motion compensation process as a motion-compensated image and cause the motion-compensated image to be displayed.

As described above, depending on an observation target, a region corresponding to an object such as a cell nucleus included in the observation target may be set as a region to be noted. In this case, the motion compensation process and an analysis process to be described below may have to be performed on an observation target region. Thus, the motion compensation unit 261 may extract not only the region to be noted but also a region including the observation target region corresponding to the region to be noted (a target region of the motion compensation process) as a motion-compensated image. Thereby, an image including the motion-compensated observation target region can be obtained.

In addition, a motion-compensated image that the motion compensation unit 261 obtains may be, for example, a motion-compensated image obtained by performing the motion compensation process on at least one observation target region included in a captured image constituting a dynamic image. Specifically, the motion compensation unit 261 may extract an image including an observation target region corresponding to a region to be noted from a captured image, and perform the motion compensation process on the extracted image. A region that is subjected to the motion compensation process may be set based on the region to be noted set by the setting unit 220. Note that center coordinates for specifying the region that is subjected to the motion compensation process can be obtained using, for example, a center point calculated based on a group of tracking points of the region to be noted.

For example, when a captured image includes images of a plurality of observation targets, and the motion compensation process is performed on the entire captured image, the motion compensation process has to be performed as many times as the number of images of the observation targets. Thus, by performing the motion compensation process on an image including an observation target region, a load of calculation caused by the motion compensation process can be reduced.

Note that a size and a shape of a motion-compensated image obtained after the motion compensation process are not particularly limited. For example, a shape of a motion-compensated image according to the present embodiment may be a rectangle.

The motion compensation unit 261 can, for example, cancel a change of an observation target region in a translation direction by performing motion compensation on a region to be noted using the motion compensation parameter corresponding to the translation component. Accordingly, a motion-compensated image indicating a state in which the observation target seems to stop without performing translation movement can be obtained.

In addition, the motion compensation unit 261 can cancel a change of the observation target region in a rotation direction by performing motion compensation on the region to be noted using the motion compensation parameter corresponding to the rotation component. Accordingly, a motion-compensated image indicating a state in which the observation target seems not to rotate can be obtained.

Furthermore, the motion compensation unit 261 can cancel a change of the observation target region in a scaling direction by performing motion compensation on the region to be noted using the motion compensation parameter corresponding to the scaling component. Accordingly, a motion-compensated image indicating a state in which the size of the observation target seems not to change can be obtained.

The motion compensation process performed by the motion compensation unit 261 is executed by solving simultaneous equations expressed by the following formulae (10) and (11) when, for example, the setting unit 220 disposes tracking points for the region to be noted and the estimation unit 230 uses the Helmert transformation formula. Here, (X, Y) represents the coordinates of each pixel of a captured image that is subjected to the motion compensation process, and (X', Y') represents the coordinates of each pixel which have undergone a coordinate transformation in the motion compensation process. The motion compensation unit 261 generates a motion-compensated image for the region to be noted that has undergone the motion compensation process from the captured image that has undergone the motion compensation process.

[Math.5]

$$X = A + \Lambda \cos \Theta \cdot X' - \Lambda \sin \Theta \cdot Y' \quad (10)$$

$$X = B + \Lambda \sin \Theta \cdot X' + \Lambda \cos \Theta \cdot Y' \quad (11)$$

Here, when the translation component is not selected in the selection of motion compensation parameters by the selection unit 250, A=0 and B=0, when the rotation component is not selected, Θ=0, and when the scaling component is not selected, Λ=1.

(Analysis Unit)

The analysis unit 262 performs an analysis process on the observation target corresponding to the region to be noted on which the motion compensation unit 261 has performed the motion compensation process. For example, the analysis unit 262 may perform a process based on a motion compensation parameter calculated by the parameter calculation unit 240.

Specifically, the analysis unit 262 may perform the analysis process using any value of the motion compensation parameters A, B, Θ, and Λ. More specifically, the analysis unit 262 may perform the analysis process on the observation target using at least any of the motion compensation parameters A and B corresponding to the translation component. Accordingly, it is possible to evaluate a motion of the observation target in the translation direction in regard to a length of locomotion, a speed of locomotion, a direction of locomotion, a history of locomotion, a vibration cycle, or the like of the observation target. In addition, the analysis unit 262 may perform the analysis process on the observation target using the motion compensation parameter Θ corresponding to the rotation component. Accordingly, a motion of the observation target in the rotation direction in regard to a rotation angle, a rotation speed, a rotation history, or the like of the observation target can be evaluated. In addition, the analysis unit 262 may perform the analysis process on the observation target using the motion compensation parameter Λ corresponding to the scaling component. Accordingly, a motion of the observation target in the scaling direction in regard to pulsation or the like of the observation target can be evaluated.

By performing the analysis process using the motion compensation parameters as described above, not only can the motion compensation process on the observation target be performed simply, but quantitative data can also be obtained.

In addition, the analysis unit 262 may perform the analysis process on a motion-compensated image generated by the motion compensation unit 261. For example, the analysis unit 262 may calculate a motion vector of an internal motion of an observation target included in a motion-compensated image using image processing. Furthermore, the analysis unit 262 may calculate a size or a shape of the observation target included in the motion-compensated image using image processing. By performing analysis on the motion-compensated image as described above, the observation target can be analyzed in a state in which a motion of the observation target is cancelled. Therefore, observation and analysis that would be difficult in a state in which the observation target locomotes autonomously or moves due to vibration of the imaging device or the like can be performed more easily and exactly.

In addition, the analysis unit 262 may analyze a region including the observation target region in the motion-compensated image. By limiting the region that is subjected to analysis, a load of the analysis process imposed on a processing circuit can be reduced. For example, when the motion-compensated image includes a plurality of observation target regions, if the entire motion-compensated image is analyzed for each of the observation target regions, a load of the analysis process imposed on the processing circuit increases. Thus, by extracting a region in which each of the observation target regions can be specified from the motion-compensated image and analyzing the region, a load of the analysis process imposed on the processing circuit can be reduced. Note that such a region that is subjected to analysis may be identified based on a region to be noted set by the setting unit 220. The region to be noted can be set to correspond to a part or all of an observation target region. Therefore, the region that is subjected to analysis can be easily specified using the region to be noted.

Note that examples of the analysis process by the analysis unit 262 will be described in application examples of the information processing device 20 in regard to results of processes.

Functions of the function units included in the processing unit 260 have been described above. Information regarding the results of the processes performed by the processing unit 260 is output to the display control unit 270.

(Display Control Unit)

The display control unit 270 controls display of the results of the processes performed by the processing unit 260. For example, the display control unit 270 causes the results of the processes to be displayed on a display device provided inside or outside the information processing device 20. The results of the processes include at least any of a motion-compensated image generated in the motion compensation process performed by the motion compensation unit 261 and at least one analysis process result by the analysis unit 262.

In addition, when the display control unit 270 controls a motion-compensated image to be displayed, the display unit may adjust an orientation of the motion-compensated image through an operation of a user, image processing, or the like. Accordingly, an observation target having the orientation that the user desires can be observed and analyzed.

In addition, the display control unit 270 may control, for example, display of a screen for allowing a user to select a motion compensation parameter. The screen can include a check box or the like for allowing the user to select a motion compensation parameter corresponding to each motion component. The selection unit 250 may output information of the motion compensation parameter selected by the user through an operation performed on the screen to the parameter calculation unit 240 or the processing unit 260. Accordingly, motion components that are subjected to the motion compensation process can be easily switched.

In addition, in regard to a motion-compensated image that has undergone the motion compensation process, the display control unit 270 may control display of the motion-compensated image. For example, the display control unit 270 may change a size, an orientation, and a scaling rate of the motion-compensated image. This display control process may be performed based on an operation of a user on the information processing device 20, or through image processing or the like based on a result of estimation of a motion of a region to be noted. For example, the display control unit 270 may control an orientation of an observation target region corresponding to a region to be noted included in a motion-compensated image to have a predetermined orientation using a magnitude of motion of the translation component of the region to be noted. Accordingly, for example, a plurality of observation target regions can be displayed with an aligned orientation on the display unit. Thus, observation targets can be compared more easily.

Note that an example of a screen displayed on the display unit by the display control unit 270 will be described below.

2.2. Process Example

The configuration example of the information processing device 20 according to an embodiment of the present disclosure has been described above. Next, an example of a process performed by the information processing device 20 according to an embodiment of the present disclosure will be described using FIGS. 10 and 11. The process performed by the information processing device 20 according to the present embodiment is constituted with a motion estimation process (S101 to S107 of FIG. 10), and a motion compensation process and an analysis process (S201 to S209 of FIG. 11).

(Estimation Process)

First, the motion estimation process performed by the information processing device 20 according to the present embodiment will be described. FIG. 10 is a flowchart showing an example of the motion estimation process performed by the information processing device 20 according to an embodiment of the present disclosure. First, the communication unit 210 acquires a dynamic image from the imaging device 10, and outputs one captured image of the dynamic image to the setting unit 220 (S101).

Next, the setting unit 220 sets a region to be noted from the one captured image (S103). Then, the setting unit 220 disposes tracking points for the set region to be noted (S105).

Next, the estimation unit 230 estimates a motion of the region to be noted based on motions of the tracking points in the dynamic image (S107). The estimation unit 230 estimates the motion of the region to be noted in at least another captured image constituting the dynamic image other than the one captured image. Accordingly, the motion of the region to be noted in the dynamic image is estimated.

(Motion Compensation Process and Analysis Process)

Next, the motion compensation process and the analysis process performed by the information processing device 20 according to the present embodiment will be described. FIG. 11 is a flowchart showing an example of the motion compensation process and the analysis process performed by the information processing device 20 according to an embodiment of the present disclosure. First, the parameter calculation unit 240 calculates motion compensation parameters based on the motion of the region to be noted estimated by the estimation unit 230 (S201). The calculated motion compensation parameters are output to the processing unit 260.

Next, the selection unit 250 selects at least one motion compensation parameter among the motion compensation parameters output to the processing unit 260 which is to be used in the process of the processing unit 260 (S203). Note that, when only one motion compensation parameter is calculated by the parameter calculation unit 240, Step S203 may be omitted.

Next, using the motion compensation parameter selected by the selection unit 250, the motion compensation unit 261 performs the motion compensation process on the dynamic image (S205). Then, the analysis unit 262 performs the analysis process on the dynamic image that has undergone the motion compensation process (motion-compensated image) (S207). Note that, when the analysis unit 262 performs no analysis process, Step S207 may be omitted.

Next, the display control unit 270 controls display of the result of the process performed by the processing unit 260 (S209). The display control unit 270 controls the display unit provided inside or outside the information processing device 20 to display, for example, at least any of the motion-compensated image generated by the motion compensation unit 261 and the result of the analysis by the analysis unit 262.

The information processing device 20 appropriately executes the processes of Steps S201 to S209 described above based on an operation of a user or the like. Accordingly, the results of the processes of the dynamic image are appropriately displayed to the user.

2.3. Application Examples

Application examples of the results of the processes by the information processing device 20 according to an embodiment of the present disclosure will be described. Here, examples of the motion compensation process and the analysis process will be described while viewing screens that the display control unit 270 causes to be displayed on the display unit provided inside or outside the information processing device 20.

Application Example 1: Motion Compensation Process and Analysis Process on a Wandering Cell First, a first application example of the information processing device 20 according to the present embodiment will be described. FIG. 12 is a diagram showing the first application example of the information processing device 20 according to the present embodiment. Referring to FIG. 12, a screen 1000 displayed on the display unit by the display control unit 270 includes an original dynamic image display screen 1010, a motion-compensated image display screen 1020, a selection screen 1021, and analysis result display screens 1030 to 1033. The original dynamic image display screen 1010 displays a dynamic image acquired from the imaging device 10. Note that the original dynamic image display screen 1010 may display a dynamic image being reproduced, or one captured image (still image) constituting the dynamic image. The motion-compensated image display screen 1020 displays a motion-compensated image generated by performing the motion compensation process on the dynamic image being displayed on the original dynamic image display screen 1010. The selection screen 1021 displays a screen for allowing a user to select a component corresponding to a motion compensation parameter to be motion-compensated by the motion compensation unit 261. The selection unit 250 may select a motion compensation parameter corresponding to a motion component whose checkbox displayed on the selection screen 1021 has been checked. The analysis result display screens 1030 to 1033 display graphs and images related to analysis results from the analysis unit 262.

The original dynamic image display screen 1010 is displaying images of a plurality of wandering cells. Among these, a wandering cell image 500 is assumed to have been selected as a processing target of the processing unit 260 through an operation of a user or the like. In this case, a frame 1011 indicating that the wandering cell image 500 has been selected may be displayed around the wandering cell image 500.

At this moment, the processing unit 260 performs the motion compensation process and the analysis process on the dynamic image including the selected wandering cell image 500. Since "Translation" and "Rotation" have been checked on the selection screen 1021, the motion compensation unit 261 performs motion compensation on the dynamic image including the wandering cell image 500 using the motion compensation parameters corresponding to the translation component and the rotation component. After the motion compensation process in regard to the translation component and the rotation component is performed, the motion-compensated image display screen 1020 displays a motion-compensated image including a wandering cell image 501.

In addition, the analysis result display screen 1030 displays a graph of a history of locomotion of the wandering cell image 500 in an XY coordinate system. The history of locomotion can be acquired from the motion compensation parameter of the translation component of the wandering cell image 500. Thereby, the motion of the wandering cell in the translation direction can be quantitatively evaluated.

Furthermore, the analysis result display screen 1031 displays a time-series graph of a rotation history of the wandering cell image 500. The rotation history can be acquired from the motion compensation parameter of the rotation component of the wandering cell image 500. Thereby, the motion of the wandering cell in the rotation direction can be quantitatively evaluated.

Furthermore, the analysis result display screen 1032 displays an image related to a change in the shape of the wandering cell image 500. This image may include the initial shape of the wandering cell image 500 (for example, the shape of the wandering cell image 500 in a captured image used for a region-to-be-noted setting process by the setting unit 220) for comparison. This image related to the change in the shape can be generated based on the motion-compensated image. Thereby, the change in the shape of the wandering cell (a degree of expansion or contraction) can be evaluated.

Furthermore, the analysis result display screen 1033 displays an image in which internal motion vectors of the wandering cell image 500 are visualized. The motion vectors can be calculated by dividing the motion-compensated image into predetermined regions and applying a technique such as block matching to each of the divided regions. By performing image processing on an observation target region that has undergone the motion compensation process in this way, a change in a form of an observation target can be identified and only the change can be analyzed.

The information processing device 20 described in the present application example analyzes an internal motion of the wandering cell through the motion compensation process and the analysis process eliminating its autonomous locomotion. Thereby, a change in an internal form of the wandering cell can be quantitatively evaluated. Further, according to the information processing device 20, a motion component that is subjected to motion compensation when the motion compensation process is performed can be selected. Thus, not only the change in the internal form of the wandering cell but also its autonomous locomotion can be evaluated.

Application Example 2: Analysis Process on Regional Change in Form of Myocardial Cell Next, a second application example of the information processing device 20 according to the present embodiment will be described. FIG. 13 is a diagram showing the second application example of the information processing device 20 according to the present embodiment. Referring to FIG. 13, a screen 1100 displayed on the display unit by the display control unit 270 includes an original dynamic image display screen 1110, motion-compensated image display screens 1120A and 1120B, and analysis result display screens 1130 to 1133.

The original dynamic image display screen 1110 displays images of a plurality of myocardial cells. Among these, myocardial cell images 510A and 510B are assumed to have been selected as processing targets of the processing unit 260 through an operation of a user or the like. In this case, regions to be noted 111A and 1111B may be set for the myocardial cell images 510A and 510B. The processing unit 260 performs the motion compensation process and the analysis process on a dynamic image including the myocardial cell images 510A and 510B. The motion-compensated image display screens 1120 display motion-compensated images each including myocardial cell images 511A and 511B.

In addition, the analysis result display screen 1130 displays a graph of a history of locomotion of the myocardial cell images 510A and 510B. The history of locomotion can be acquired from the motion compensation parameter of the translation component of the myocardial cell images 510A and 510B. Thereby, motions of the myocardial cells can be quantitatively evaluated.

Furthermore, the analysis result display screen 1131 displays graphs showing sizes of the motions caused by pulsation of the myocardial cell images 510A and 510B and time-series changes in areas of the images. The graphs with regard to the sizes of the motions based on the pulsation and the areas of the images can be obtained based on calculation results of motion vectors of the motion-compensated images. Thereby, pulsation of the myocardial cells can be quantitatively evaluated with high accuracy.

Furthermore, the analysis result display screens 1132 and 1133 display images with regard to changes in shapes and scaling rates of the myocardial cell images 510A and 510B. The scaling rates can be calculated from the motion compensation parameter corresponding to the scaling component of the myocardial cell images 510A and 510B. Thereby, contraction and expansion motions of the myocardial cells can be quantitatively evaluated.

The information processing device 20 introduced in the present application example extracts scaling movements of the plurality of myocardial cells and analyzes time-series data of the scaling movements and the changes in their areas through the motion compensation process and the analysis process. Thereby, a change in a pulsation state of individual myocardial cells or the like resulting from drug efficacy can be evaluated from more diverse perspectives.

Application Example 3: Analysis Process on Mobility of Plurality of Sperms

Next, a third application example of the information processing device 20 according to the present embodiment will be described. FIG. 14 is a diagram showing the third application example of the information processing device 20 according to the present embodiment. Referring to FIG. 14, a screen 1200 displayed on the display unit by the display control unit 270 includes an original dynamic image display screen 1210, motion-compensated image display screens 1220A to 1220D, and analysis result display screens 1230 to 1233.

The original dynamic image display screen 1210 displays images of a plurality of sperms. Among these, sperm images 520A to 520D are assumed to have been selected as processing targets of the processing unit 260 through an operation of a user or the like. In this case, frames 1211A to 1211D indicating that the sperm images 520A to 520D have been selected and may be displayed around each of the sperm images 520A to 520D.

At this time, the processing unit 260 performs the motion compensation process and the analysis process on each of the selected sperm images 520A to 520D of a dynamic image. The motion-compensated image display screens 1220A to 1220D each display dynamic images including sperm images 521A to 521D on which the motion compensation process has been performed with regard to the translation component and the rotation component. Note that, as shown in FIG. 14, the display control unit 270 may control an orientation of each motion-compensated image or the like so that the sperm images 521A to 521D have the same orientation. For example, the display control unit 270 may estimate directions of locomotion of the sperm images 520A to 520D from magnitude of motion of translation components of the sperm images 520A to 520D, and control display of each motion-compensated image such that the estimated directions of locomotion are aligned to have the defined orientation on the motion-compensated image display screens 1220A to 1220D. Thereby, forms such as sizes or shapes of the sperm images 521A to 521D can be compared to each other.

In addition, the analysis result display screen 1230 and the analysis result display screen 1231 respectively display graphs with regard to histories of locomotion and rotation histories of the sperm images 520A to 520D. The histories of locomotion can be acquired from the motion compensation parameters of the translation components of the sperm images 520A to 520D. In addition, the rotation histories can be acquired from the motion compensation parameters of the rotation components of the sperm images 520A to 520D. Thereby, motions of the sperms in the translation directions and the rotation directions can be quantitatively evaluated.

Furthermore, the analysis result display screen 1232 displays a bar graph showing amounts of locomotion of the sperm images 520A to 520D. The amounts of locomotion can be calculated from the motion compensation parameters of the translation components of the sperm images 520A to 520D. By displaying the amounts of locomotion of the sperms using the bar graph, movement states of the sperms can be quantitatively analyzed.

Furthermore, the analysis result display screen 1233 displays a bar graph showing evaluation values of forms of the sperm images 521A to 521D. The evaluation values of the forms may be ones calculated from, for example, characteristics of sizes or shapes of the sperm images 521A to 521D. By displaying the evaluation values of the forms of the sperms, quality of the forms of the sperms can be quantitatively evaluated.

The information processing device 20 introduced in the present application example aligns the images of the plurality of sperms in the same orientation through the motion compensation process, analyzes movements and forms of the sperms, and displays results of the analysis. Accordingly, it is possible to understand states of the individual sperms quantitatively and relatively. Therefore, in sampling of sperms, for example, sperms in their best conditions can be selected based on quantitative information.

Note that it is needless to say that screens displayed by the display control unit 270 are not limited to the screens displaying the information related to the results of the processes of the information processing device 20 described above. For example, the display control unit 270 may cause only screens that display motion-compensated images to be displayed, or only the screens that display analysis results. In addition, screens that display results of processes of the processing unit 260 may be displayed on the same screen in parallel, or on different screens.

2.4. Effect

The configuration example, process example, and application examples of the information processing device 20 according to an embodiment of the present disclosure have been described above. The information processing device 20 according to the present embodiment estimates a motion of a region to be noted in a dynamic image, and performs the motion compensation process and the analysis process on the dynamic image using motion compensation parameters calculated based on the motion. With this configuration, a motion-compensated image in which a motion of an observation target is fixed in at least one of a translation direction, a rotation direction, and a scaling direction can be obtained. Since the motion of the observation target can be caused to stop in a relative point of view, a change in the form of the observation target can be analyzed exactly. Thus, even if a cell is moving actively, a dynamic image of the cell in which it seems to stop can be obtained. Therefore, a change in an internal from of a cell that was difficult to observe in the past can be observed and analyzed exactly.

In addition, the information processing device 20 according to the present embodiment can select a motion compensation parameter to be used in the motion compensation process. Accordingly, an optimum method for observing and analyzing a change in a form of an observation target can be changed according to an observation purpose or an analysis purpose for the observation target. Therefore, the observation target can be evaluated from more various perspectives.

3. HARDWARE CONFIGURATION EXAMPLE

Next, with reference to FIG. 15, a hardware configuration of an information processing device according to an embodiment of the present disclosure is described. FIG. 15 is a block diagram showing a hardware configuration example of the information processing device according to the embodiment of the present disclosure. An illustrated information processing device 900 can realize the information processing device 20 in the above described embodiment.

The information processing device 900 includes a central processing unit (CPU) 901, read only memory (ROM) 903, and random access memory (RAM) 905. In addition, the information processing device 900 may include a host bus 907, a bridge 909, an external bus 911, an interface 913, an input device 915, an output device 917, a storage device 919, a drive 921, a connection port 925, and a communication device 929. The information processing device 900 may include a processing circuit such as a digital signal processor (DSP) or an application-specific integrated circuit (ASIC), instead of or in addition to the CPU 901.

The CPU 901 functions as an arithmetic processing device and a control device, and controls the overall operation or a part of the operation of the information processing device 900 according to various programs recorded in the ROM 903, the RAM 905, the storage device 919, or a removable recording medium 923. For example, the CPU 901 controls overall operations of respective function units included in the information processing device 20 of the above-described embodiment. The ROM 903 stores programs, operation parameters, and the like used by the CPU 901. The RAM 905 transiently stores programs used when the CPU 901 is executed, and parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input device 915 is a device operated by a user such as a mouse, a keyboard, a touchscreen, a button, a switch, and a lever. The input device 915 may be a remote control device that uses, for example, infrared radiation and another type of radio waves. Alternatively, the input device 915 may be an external connection device 927 such as a mobile phone that corresponds to an operation of the information processing device 900. The input device 915 includes an input control circuit that generates input signals on the basis of information which is input by a user to output the generated input signals to the CPU 901. The user inputs various types of data and indicates a processing operation to the information processing device 900 by operating the input device 915.

The output device 917 includes a device that can visually or audibly report acquired information to a user. The output device 917 may be, for example, a display device such as a LCD, a PDP, and an OELD, an audio output device such as a speaker and a headphone, and a printer. The output device 917 outputs a result obtained through a process performed by the information processing device 900, in the form of text or video such as an image, or sounds such as audio sounds.

The storage device 919 is a device for data storage that is an example of a storage unit of the information processing device 900. The storage device 919 includes, for example, a magnetic storage device such as a hard disk drive (HDD), a semiconductor storage device, an optical storage device, or a magneto-optical storage device. The storage device 919 stores therein the programs and various data executed by the CPU 901, and various data acquired from an outside.

The drive 921 is a reader/writer for the removable recording medium 923 such as a magnetic disk, an optical disc, a magneto-optical disk, and a semiconductor memory, and built in or externally attached to the information processing device 900. The drive 921 reads out information recorded on the mounted removable recording medium 923, and outputs the information to the RAM 905. The drive 921 writes the record into the mounted removable recording medium 923.

The connection port 925 is a port used to directly connect devices to the information processing device 900. The connection port 925 may be a Universal Serial Bus (USB) port, an IEEE1394 port, or a Small Computer System Interface (SCSI) port, for example. The connection port 925 may also be an RS-232C port, an optical audio terminal, a High-Definition Multimedia Interface (HDMI (registered trademark)) port, and so on. The connection of the external connection device 927 to the connection port 925 makes it possible to exchange various kinds of data between the information processing device 900 and the external connection device 927.

The communication device 929 is a communication interface including, for example, a communication device for connection to a communication network NW. The communication device 929 may be, for example, a wired or wireless local area network (LAN), Bluetooth (registered trademark), or a communication card for a wireless USB (WUSB). The communication device 929 may also be, for example, a router for optical communication, a router for asymmetric digital subscriber line (ADSL), or a modem for various types of communication. For example, the communication device 929 transmits and receives signals in the Internet or transits signals to and receives signals from another communication device by using a predetermined protocol such as TCP/IP. The communication network NW to which the communication device 929 connects is a network established through wired or wireless connection. The communication network NW is, for example, the Internet, a home LAN, infrared communication, radio wave communication, or satellite communication.

The example of the hardware configuration of the information processing device 900 has been introduced.

4. CONCLUSION

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

For example, although the information processing system 1 is configured to be provided with the imaging device 10 and information processing device 20 in the above-described embodiment, the present technology is not limited thereto. For example, the imaging device 10 may have the function of the information processing device 20 (the motion estimation function, the motion compensation function, and the analysis function). In this case, the information processing system 1 is realized by the imaging device 10. In addition, the information processing device 20 may have the function of the imaging device 10 (imaging function). In this case, the information processing system 1 is realized by the information processing device 20. Further, the imaging device 10 may have a part of the function of the information processing device 20, and the information processing device 20 may have a part of the function of the imaging device 10.

In addition, although cells and micro-organisms have been exemplified as observation targets in analysis by the information processing system 1 in the above-described embodiment, the present technology is not limited thereto. For example, the observation target may be a cell organelle, a biological tissue, an organ, a human, an animal, a plant, a non-living structure, or the like. Changes in forms of these observation targets can also be observed and analyzed exactly using the information processing system 1.

The steps in the processes performed by the information processing device in the present specification may not necessarily be processed chronologically in the orders described in the flowcharts. For example, the steps in the processes performed by the information processing device may be processed in different orders from the orders described in the flowcharts or may be processed in parallel.

Also, a computer program causing hardware such as the CPU, the ROM, and the RAM included in the information processing device to carry out the equivalent functions as the above-described configuration of the information processing device can be generated. Also, a storage medium having the computer program stored therein can be provided.

In addition, the effects described in the present specification are merely illustrative and demonstrative, and not limitative. In other words, the technology according to embodiments of the present disclosure can exhibit other effects that are evident to those skilled in the art along with or instead of the effects based on the present specification.

Additionally, the present technology may also be configured as below.

(1)

An information processing device including:

a setting unit that sets at least one region to be noted from one captured image constituting a dynamic image of a biological sample;

an estimation unit that estimates a motion of the at least one region to be noted in the dynamic image;

a parameter calculation unit that calculates a motion compensation parameter based on the motion;

a processing unit that performs a process on the at least one region to be noted using the motion compensation parameter; and a display control unit that controls display of a result of the process.

(2)

The information processing device according to (1), further including:

a selection unit that selects the motion compensation parameter to be used in the process performed by the processing unit.

(3)

The information processing device according to (2), wherein the parameter calculation unit calculates a plurality of motion compensation parameters based on the motion, and the selection unit selects at least one motion compensation parameter among the plurality of motion compensation parameters.

(4)

The information processing device according to (2) or (3), wherein the selection unit selects the motion compensation parameter calculated by the parameter calculation unit.

(5)

The information processing device according to any one of (2) to (4), wherein the estimation unit estimates a size of at least one motion component constituting the motion, and the parameter calculation unit calculates the motion compensation parameter corresponding to the at least one motion component based on the size of the at least one motion component.

(6)

The information processing device according to (5), wherein the motion component includes at least one of a translation component, a rotation component, and a scaling component.

(7)

The information processing device according to any one of (1) to (6), wherein, as the process, the processing unit performs a motion compensation process on the dynamic image including a region equivalent to the biological sample corresponding to the at least one region to be noted using the motion compensation parameter.

(8)

The information processing device according to (7), wherein the display control unit causes a motion-compensated image generated through the motion compensation process on the dynamic image to be displayed.

(9)

The information processing device according to (8), wherein the display control unit controls display of the motion-compensated image based on the estimated motion of the region to be noted.

(10)

The information processing device according to any one of (7) to (9), wherein, as the process, the processing unit performs an analysis process on the biological sample corresponding to the region to be noted.

(11)

The information processing device according to (10), wherein the analysis process includes an analysis process based on the motion compensation parameter.

(12)

The information processing device according to (10) or (11), wherein the analysis process includes an analysis process on a motion-compensated image generated through the motion compensation process.

(13)

The information processing device according to any one of (10) to (12), wherein the display control unit causes a result of the analysis process to be displayed.

(14)

The information processing device according to any one of (2) to (13), wherein the selection unit selects the motion compensation parameter based on at least one of a type of the biological sample corresponding to the at least one region to be noted and an analysis method for the biological sample.

(15)

The information processing device according to any one of (1) to (14), wherein the setting unit disposes a plurality of tracking points for the at least one set region to be noted in the one captured image, and the estimation unit estimates the motion based on movement positions of the plurality of tracking points.

(16)

The information processing device according to (15), wherein the estimation unit estimates the motion based on a group of motion vectors corresponding to the plurality of tracking points.

(17)

The information processing device according to any one of (1) to (16), wherein the setting unit sets a predetermined region of the captured image of the biological sample as the at least one region to be noted according to a type of the biological sample.

(18)

An information processing method performed by a processor, the method including:

setting at least one region to be noted from one captured image constituting a dynamic image of a biological sample;

estimating a motion of the at least one region to be noted in the dynamic image; calculating a motion compensation parameter based on the motion;

performing a process on the at least one region to be noted using the motion compensation parameter; and controlling display of a result of the process.

(19)

A program causing a computer to function as:

a setting unit that sets at least one region to be noted from one captured image constituting a dynamic image of a biological sample;

an estimation unit that estimates a motion of the at least one region to be noted in the dynamic image;

a parameter calculation unit that calculates a motion compensation parameter based on the motion;

a processing unit that performs a process on the at least one region to be noted using the motion compensation parameter; and a display control unit that controls display of a result of the process.

(20)

An information processing system including:

an imaging device that is provided with an imaging unit that generates a dynamic image for a biological sample; and an information processing device that is provided with a setting unit that sets at least one region to be noted from one captured image constituting the dynamic image, an estimation unit that estimates a motion of the at least one region to be noted in the dynamic image, a parameter calculation unit that calculates a motion compensation parameter based on the motion, a processing unit that performs a process on the at least one region to be noted using the motion compensation parameter, and a display control unit that controls display of a result of the process.

(21)

An information processing device including:

circuitry configured to:

set at least one region of an image of a biological sample;

select a motion compensation parameter calculated based at least on a motion of the at least one region; and control display of a result of performing a process on the at least one region using the selected motion compensation parameter.

(22)

The information processing device according to (21), wherein setting the at least one region further comprises setting the at least one region based on a type of the biological sample, and/or wherein selecting the motion compensation parameter further comprises selecting the motion compensation parameter based on the type of the biological sample.

(23)

The information processing device according to (22), wherein the type of the biological sample is determined automatically based on at least one characteristic of the biological sample.

(24)

The information processing device according to (22) wherein the circuitry is further configured to receive user input identifying the type of the biological sample.

(25)

The information processing device according to (21) wherein the circuitry is further configured to estimate a motion of the at least one region from a plurality of images of the biological sample and calculate at least one motion compensation parameter based on the estimated motion, and performing the process on the at least one region further comprises using the at least one motion compensation parameter.

(26)

The information processing device according to (25), wherein the circuitry is further configured to calculate a plurality of motion compensation parameters based on the estimated motion, and wherein selecting the motion compensation parameter further comprises selecting at least one motion compensation parameter from among the plurality of motion compensation parameters.

(27)

The information processing device according to (25), wherein selecting the motion compensation parameter further comprises selecting the calculated motion compensation parameter.

(28)

The information processing device according to (25), wherein the circuitry is further configured to estimate a size of at least one motion component corresponding to the estimated motion, and calculating the motion compensation parameter further comprises calculating the motion compensation parameter based on the size of the at least one motion component.

(29)

The information processing device according to (28), wherein the at least one motion component includes at least one of a translation component, a rotation component, and a scaling component.

(30)

The information processing device according to (21), wherein the circuitry is further configured to perform a motion compensation process on a dynamic image using the motion compensation parameter, wherein the dynamic image includes a region equivalent to the biological sample corresponding to the at least one region.

(31)

The information processing device according to (30), wherein the circuitry is further configured to control display of a motion-compensated image generated by the motion compensation process.

(32)

The information processing device according to (31), wherein the circuitry is further configured to estimate a motion of the at least one region from a plurality of images of the biological sample and control display of the motion-compensated image based on the estimated motion of the at least one region.

(33)

The information processing device according to any one of (30), wherein the motion compensation process includes performing an analysis process on the biological sample corresponding to the at least one region.

(34)

The information processing device according to (33), wherein the analysis process includes an analysis process based on the motion compensation parameter.

(35)

The information processing device according to (33), wherein the analysis process includes an analysis process on a motion-compensated image generated through the motion-compensation process.

(36)

The information processing device according to (33), wherein the circuitry is further configured to control display of a result of the analysis process.

(37)

The information processing device according to (21), wherein selecting the motion compensation parameter further comprises selecting the motion compensation parameter based on at least one of the type of the biological sample and an analysis method for the biological sample.

(38)

The information processing device according to (21), wherein the circuitry is further configured to dispose a plurality of tracking points for the at least one region in the image and to estimate the motion of the at least one region based on movement positions of the plurality of tracking points.

(39)

The information processing device according to (38), wherein the circuitry is further configured to estimate the motion of the at least one region based on a group of motion vectors corresponding to the plurality of tracking points.

(40)

The information processing device according to (21), wherein the circuitry is further configured to set a predetermined region of the image of the biological sample as the at least one region according to the type of the biological sample.

(41)

An information processing method performed by a processor, the method including: setting at least one region of an image of a biological sample;

selecting a motion compensation parameter calculated based at least on a motion of the at least one region; and controlling display of a result of performing a process on the at least one region using the selected motion compensation parameter.

(42) At least one computer-readable storage medium storing computer-executable instructions that, when executed, perform a method including:

setting at least one region of an image of a biological sample;

selecting a motion compensation parameter calculated based at least on a motion of the at least one region; and controlling display of a result of performing a process on the at least one region using the selected motion compensation parameter.

(43) An information processing system including:

an imaging device configured to generate an image of a biological sample; and circuitry configured to:

set at least one region of an image of a biological sample;

select a motion compensation parameter calculated based at least on a motion of the at least one region; and control display of a result of performing a process on the at least one region using the selected motion compensation parameter.

REFERENCE SIGNS LIST 1 information processing system
10 imaging device
20 information processing device
210 communication unit
220 setting unit
230 estimation unit
240 parameter calculation unit
250 selection unit
260 processing unit
261 motion compensation unit
262 analysis unit
270 display control unit

The invention claimed is:

1. An information processing device comprising:
circuitry configured to:
set at least one region of an image of a biological sample;
estimate a motion of the at least one region from a plurality of images of the biological sample;
calculate at least one motion compensation parameter based on the estimated motion and a type of the biological sample;
select a motion compensation parameter of the at least one motion compensation parameter; and
control display of a result of performing a process on the at least one region using the selected motion compensation parameter.

2. The information processing device according to claim 1, wherein setting the at least one region further comprises setting the at least one region based on the type of the biological sample.

3. The information processing device according to claim 1, wherein the type of the biological sample is determined automatically based on at least one characteristic of the biological sample.

4. The information processing device according to claim 1, wherein the circuitry is further configured to receive user input identifying the type of the biological sample.

5. The information processing device according to claim 1, wherein the circuitry is further configured to calculate a plurality of motion compensation parameters based on the estimated motion, and wherein selecting the motion compensation parameter further comprises selecting the motion compensation parameter from among the plurality of motion compensation parameters.

6. The information processing device according to claim 1, wherein the circuitry is further configured to estimate a size of at least one motion component corresponding to the estimated motion, and calculating the at least one motion compensation parameter further comprises calculating the at least one motion compensation parameter based on the size of the at least one motion component.

7. The information processing device according to claim 6, wherein the at least one motion component includes at least one of a translation component, a rotation component, and a scaling component.

8. The information processing device according to claim 1, wherein the circuitry is further configured to perform a motion compensation process on a dynamic image using the selected motion compensation parameter, wherein the dynamic image includes a region equivalent to the biological sample corresponding to the at least one region.

9. The information processing device according to claim 8, wherein the circuitry is further configured to control display of a motion-compensated image generated by the motion compensation process.

10. The information processing device according to claim 9, wherein the circuitry is further configured to estimate a motion of the at least one region from a plurality of images of the biological sample and control display of the motion-compensated image based on the estimated motion of the at least one region.

11. The information processing device according to claim 8, wherein the motion compensation process includes performing an analysis process on the biological sample corresponding to the at least one region.

12. The information processing device according to claim 11, wherein the analysis process includes an analysis process based on the selected motion compensation parameter.

13. The information processing device according to claim 11, wherein the analysis process includes an analysis process on a motion-compensated image generated through the motion compensation process.

14. The information processing device according to claim 11, wherein the circuitry is further configured to control display of a result of the analysis process.

15. The information processing device according to claim 1, wherein selecting the motion compensation parameter further comprises selecting the motion compensation parameter based on an analysis method for the biological sample.

16. The information processing device according to claim 1, wherein the circuitry is further configured to dispose a plurality of tracking points for the at least one region in the image and to estimate the motion of the at least one region based on movement positions of the plurality of tracking points.

17. The information processing device according to claim 16, wherein the circuitry is further configured to estimate the motion of the at least one region based on a group of motion vectors corresponding to the plurality of tracking points.

18. The information processing device according to claim 1, wherein the circuitry is further configured to set a predetermined region of the image of the biological sample as the at least one region according to the type of the biological sample.

19. An information processing method performed by a processor, the method comprising:
    setting at least one region of an image of a biological sample;
    estimating a motion of the at least one region from a plurality of images of the biological sample;
    calculating at least one motion compensation parameter based on the estimated motion and a type of the biological sample;
    selecting a motion compensation parameter of the at least one motion compensation parameter; and
    controlling display of a result of performing a process on the at least one region using the selected motion compensation parameter.

20. At least one computer-readable storage medium storing computer-executable instructions that, when executed, perform a method comprising:
    setting at least one region of an image of a biological sample;
    estimating a motion of the at least one region from a plurality of images of the biological sample;
    calculating at least one motion compensation parameter based on the estimated motion and a type of the biological sample;
    selecting a motion compensation parameter of the at least one motion compensation parameter; and
    controlling display of a result of performing a process on the at least one region using the selected motion compensation parameter.

21. An information processing system comprising:
    an imaging device configured to generate an image of a biological sample; and
    circuitry configured to:
        set at least one region of an image of a biological sample;
        estimate a motion of the at least one region from a plurality of images of the biological sample;
        calculate at least one motion compensation parameter based on the estimated motion and a type of the biological sample;
        select a motion compensation parameter of the at least one motion compensation parameter; and
        control display of a result of performing a process on the at least one region using the selected motion compensation parameter.

* * * * *